United States Patent [19]

Hungerford et al.

[11] Patent Number: 5,172,332

[45] Date of Patent: *Dec. 15, 1992

[54] AUTOMATIC FLUID SAMPLING AND MONITORING APPARATUS AND METHOD

[75] Inventors: William G. Hungerford, Medina; Donald L. Miller; Carl Griffith, both of Middleport; Donald Kaiser, Clarence Center, all of N.Y.

[73] Assignee: American Sigma, Inc., Medina, N.Y.

[*] Notice: The portion of the term of this patent subsequent to Feb. 5, 2009 has been disclaimed.

[21] Appl. No.: 612,832

[22] Filed: Nov. 13, 1990

Related U.S. Application Data

[63] Continuation-in-part of Ser. No. 455,981, Dec. 22, 1989.

[51] Int. Cl.[5] .............................................. G01N 1/00
[52] U.S. Cl. .................................. 364/510; 73/863.01
[58] Field of Search ................. 364/510; 141/130, 94, 141/91, 89, 1; 73/863.03, 863.02, 863.01, 863, 864.34

[56] References Cited

U.S. PATENT DOCUMENTS

| | | | |
|---|---|---|---|
| 3,507,156 | 2/1968 | Merrill, Jr. | 73/863.02 |
| 3,727,464 | 4/1973 | Rutkowski et al. | 73/863.01 |
| 3,838,719 | 10/1974 | Lederer | 141/284 |
| 3,927,701 | 12/1975 | Lederer | 141/98 |
| 3,929,017 | 12/1975 | Kowalski | 364/510 X |
| 3,996,786 | 12/1976 | Mead et al. | 73/53 X |
| 4,022,059 | 5/1977 | Schontzler et al. | 141/130 X |
| 4,221,127 | 9/1980 | McClure | 73/861 |
| 4,660,422 | 4/1987 | Eads et al. | 73/863.02 |
| 4,660,607 | 4/1987 | Griffith et al. | 141/1 |
| 4,697,462 | 10/1987 | Daube, Jr. et al. | 73/862.02 X |
| 4,766,550 | 8/1988 | Byers et al. | 73/863.01 X |
| 4,799,169 | 1/1989 | Mims | 73/510 |

OTHER PUBLICATIONS

"A Programmable Calculator Improves Automatic Sampling of Suspended Sediment" by Eads et al., application file wrapper for U.S. Pat. No. 4,660,422 issued Apr. 28, 1987.

*Primary Examiner*—Parshotam S. Lall
*Assistant Examiner*—S. A. Melnick
*Attorney, Agent, or Firm*—Irving Weiner; Pamela S. Burt; Joseph P. Carrier

[57] ABSTRACT

An automatic fluid sampling and monitoring apparatus provided as a unitary structure, and capable of collecting fluid samples at selected intervals, monitoring the level of a condition of the fluid at selected intervals, and collecting and storing sampling and fluid condition data for later retrieval. Sampling operations may be controlled on the basis of time and/or levels of a fluid condition being monitored. Where the apparatus also incorporates an internal flow measuring assembly, or is connected with an external flow meter, sampling operations may also be controlled on the basis of flow rate. The apparatus includes a self-contained microprocessor for automatically controlling sampling operations, calculating fluid condition levels on the basis of signals from a sensor, and storing data relating to sample collection and the fluid condition. Stored data can be called up on a display of the apparatus, or transferred via a portable transfer unit to an external output device, such as a printer, for producing a hard copy of the data.

29 Claims, 23 Drawing Sheets

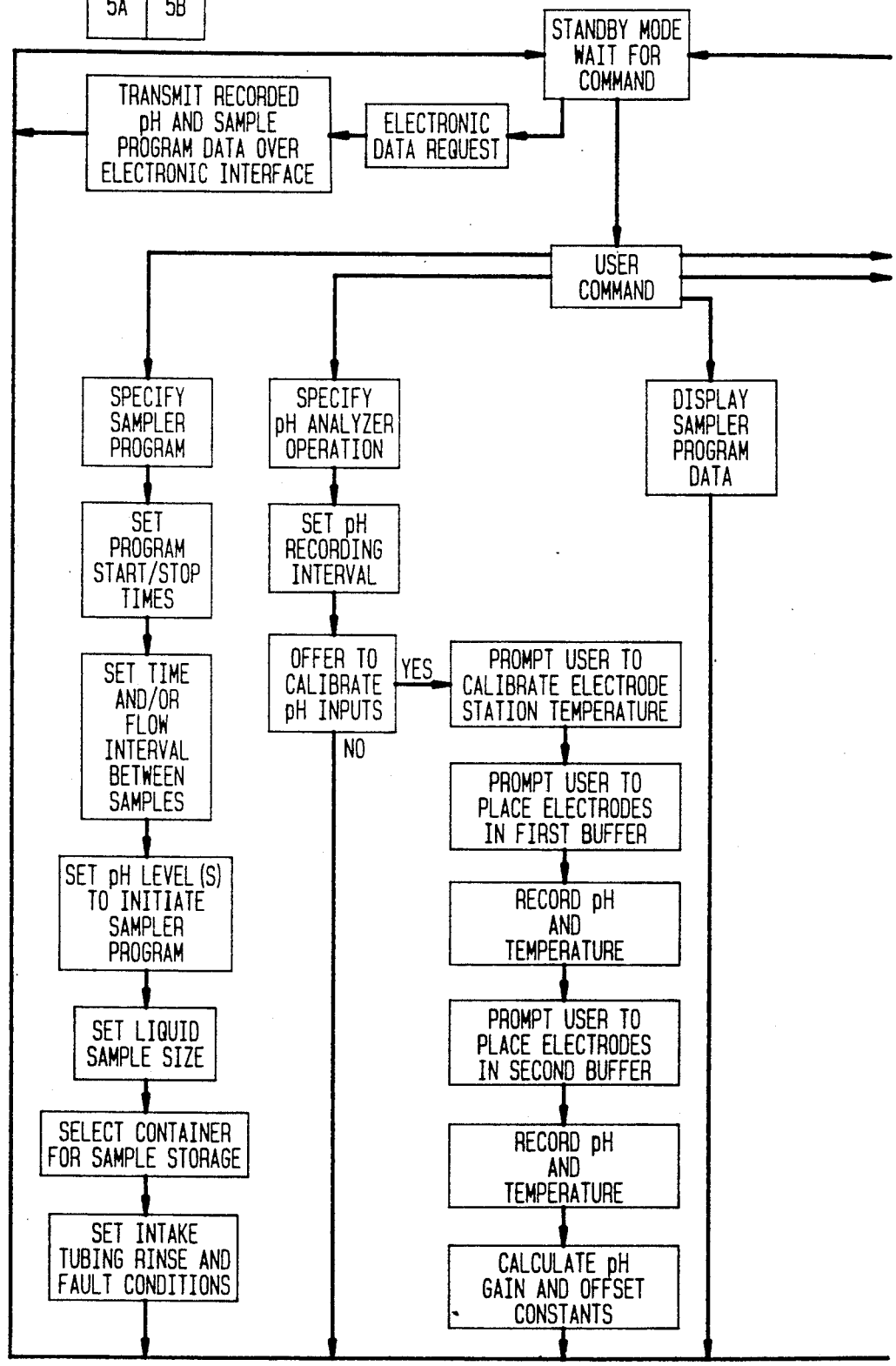

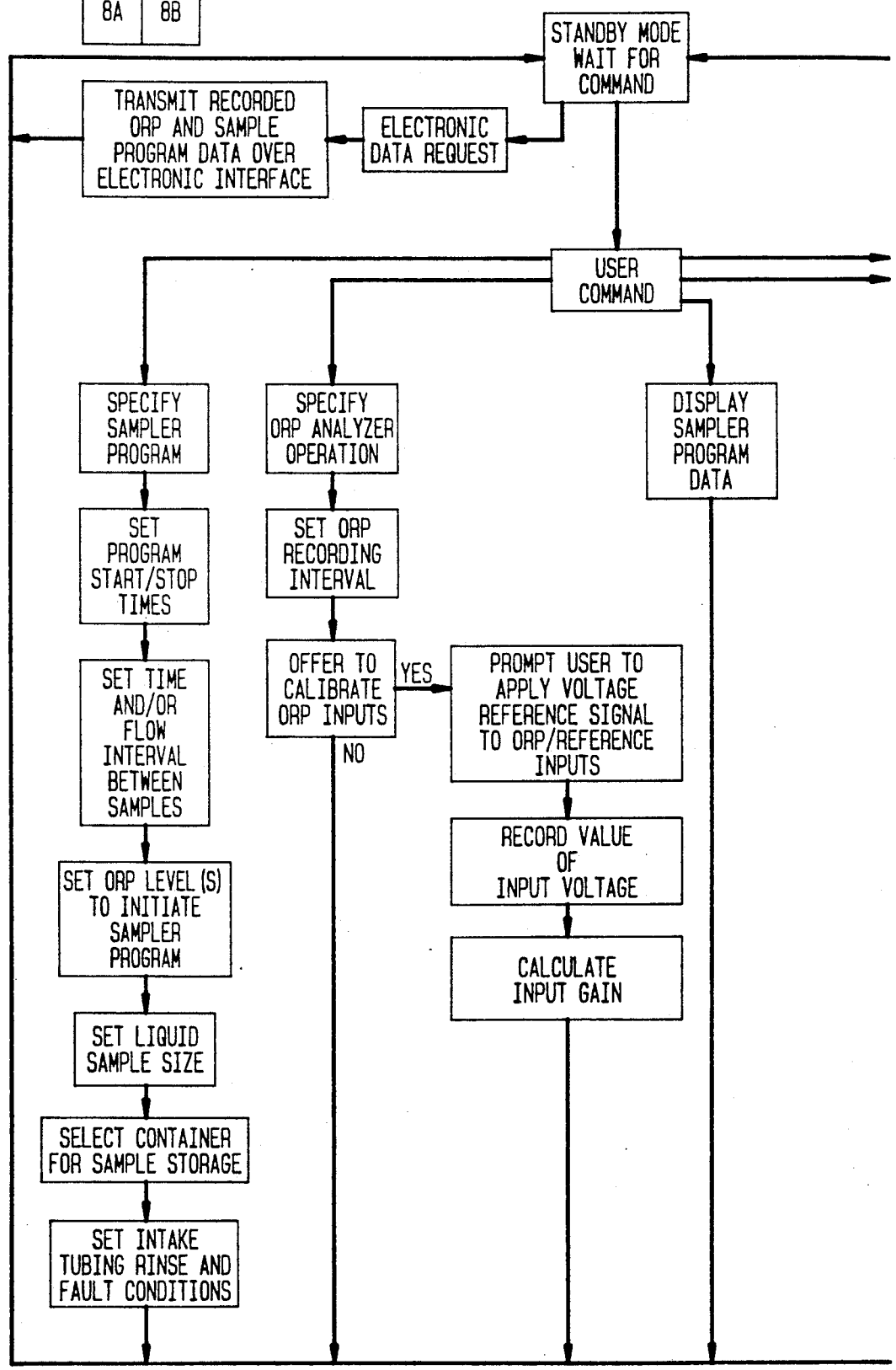

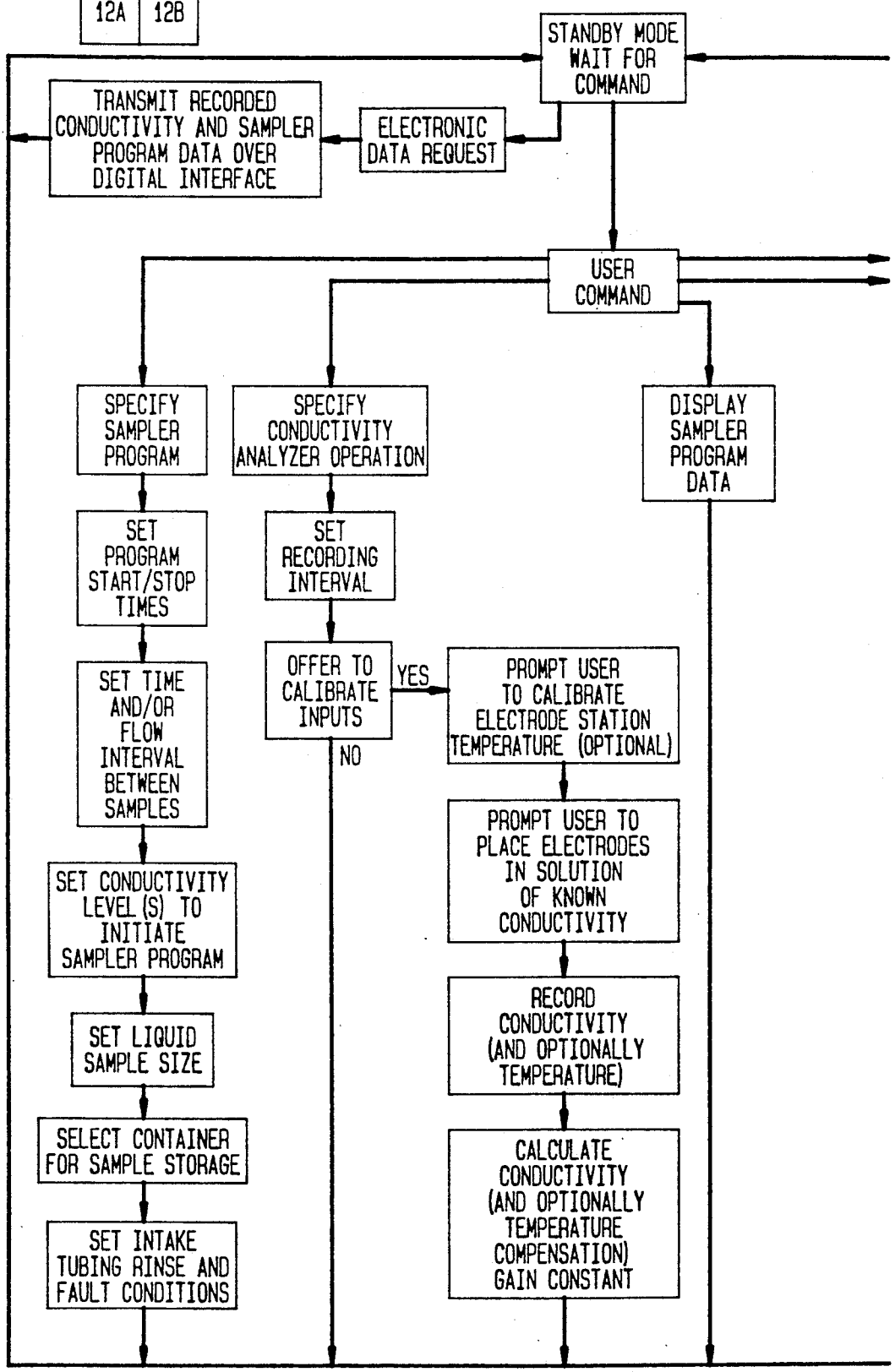

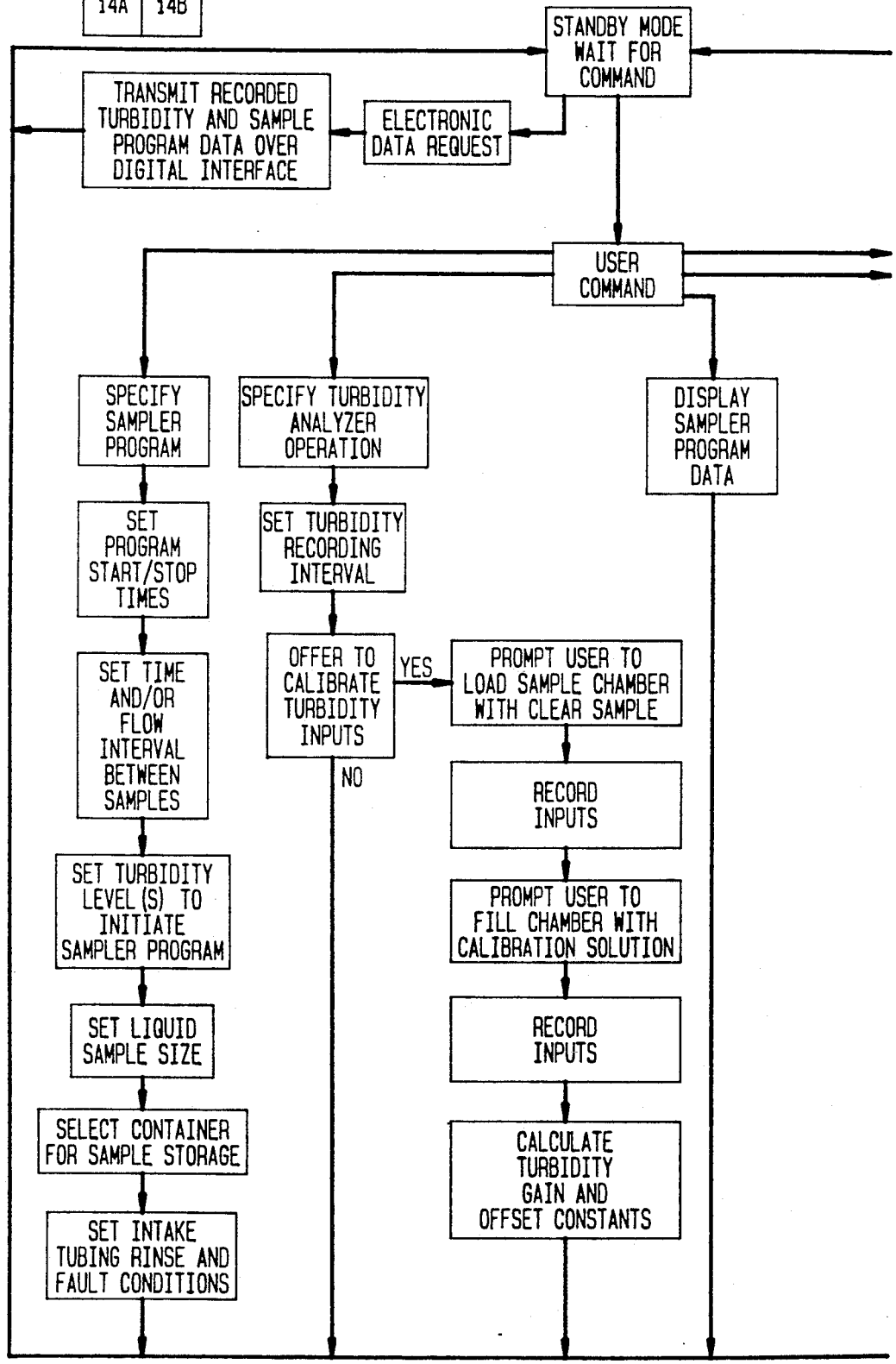

AUTOMATIC FLUID SAMPLING AND MONITORING APPARATUS AND METHOD

This is a continuation-in-part of application Ser. No. 455,981 filed Dec. 22, 1989 now U.S. Pat. No. 5,091,863.

BACKGROUND OF THE INVENTION

1. Field of the Invention

The present invention relates generally to an integrated automatic sampling and monitoring apparatus capable both of automatically performing fluid sampling operations and of automatically monitoring one or more conditions of the fluid.

More particularly, the invention relates to a compact unitary fluid sampling apparatus having a computer control system which automatically controls sampling and also calculates the value of a given fluid condition, such as pH level, on the basis of input from a sensor. By virtue of such novel arrangement, the apparatus of the invention provides the unique capability of triggering sampling operations on the basis of critical levels of a given fluid condition, such as automatically triggering sample collection to begin when pH level falls outside a pre-set acceptable range. The apparatus also automatically stores sample collection data and calculated levels of a given fluid condition, and permits sampling operations to be controlled on the basis of time as well as the detected level of the fluid condition. The stored data can be retrieved by displaying same on an alphanumeric display of the apparatus, and/or by transferring the data via a portable transfer unit to a remote output device such as a printer to provide a hard copy of the data.

The term "conditions" as employed herein is intended to connote various conditions of a fluid, i.e., physical and/or chemical properties thereof, which may be analytically measured for monitoring purposes and/or for triggering sampling operations. Such conditions include, but are not limited to, pH level, oxidation reduction potential ("ORP"), temperature, solution conductivity or resistivity, salinity, the activity of specific ions other than hydrogen ("pION"), dissolved oxygen, and/or turbidity. Monitoring of such conditions complements sampling operations of the apparatus not only with respect to tracking the history of a given condition in a process stream, but also with respect to controlling sampling operations on the basis of predetermined levels or values of given condition(s).

2. Description of the Relevant Art

In today's climate of deep concern over environmental pollution, municipal agencies and private organizations alike are faced with the responsibility of carefully monitoring fluid waste, especially in order to comply with stringent statutory and regulatory pollution limits or to conduct pollution research. To this end, an automatic fluid sampling apparatus is commonly used to monitor the composition of fluid waste by repeatedly collecting samples for subsequent laboratory analysis. In addition, a separate analytical meter may be used for on-site monitoring of a critical fluid condition, such as pH level, to alert the user in a relatively immediate fashion to an upset in the process stream. A separate flow meter may also be used for monitoring the volume of fluid flow and for pacing the sampling operations in proportion to flow rate. The sampler, analytical meter and/or flowmeter are regularly transported to remote field sites for research purposes, or are positioned in municipal or industrial manholes to monitor sewer lines containing fluid waste.

Various problems arise in transporting the separate sampler and meter devices for use at a remote field site, or in mounting the separate devices in a sewer manhole. Transporting a number of separate devices to a remote sampling site is cumbersome and inconvenient. On the other hand, mounting of the separate devices in a manhole, such as commonly required in municipal and industrial situations, presents additional difficulties. The close confines of the manhole severely restricts manipulation of the devices, so that positioning and mounting of the separate devices often proves difficult, and sometimes impossible. The operator must repeatedly enter and re-enter the manhole to separately retrieve and position each device. The devices must often be mounted one above the other, so that access to and removal of the lower device(s) is blocked by the upper device(s). Removal of the devices after monitoring is completed is often as awkward and time consuming as mounting them.

Another problem which arises with known samplers is the inability to obtain a hard copy of sample collection data, e.g., times and dates of collected and/or missed samples and parameters of the sampling program such as the volume of the collected sample, the interval between samples, and time or flow units remaining until the next sample. To comply with federal and state requirements, it is important that a record be kept of sample collection and other data. With known sampler and meter devices, the only means by which such a record can be obtained is by recording the data by hand when it appears temporarily on a display of the device. This limitation leads to inaccurate or incomplete records at best, and no hard copy of the data at worst.

The present inventors, in their prior U.S. patent application Ser. No. 455,981 filed Dec. 22, 1989, have overcome many of the problems associated with using separate samplers and flow meters by providing an integrated, compact automatic liquid sampling and flow measuring apparatus capable of pacing sampling in proportion to flow rate, and of storing sample collection and flow data for retrieval in hard copy form.

The integrated automatic sampling and monitoring apparatus of the present invention, which also has a compact structure, overcomes the problems particularly associated with separate automatic sampler and analytical meter devices. By combining a sampler and analytical meter in a single unitary structure, a number of advantages are attained. The elimination of a separate second device reduces the size and weight of the equipment, facilitating transport to remote sites and mounting in limited spaces. Further, because the sampler and analytical meter share the same microprocessor, digital display, keyboard, circuitry, etc., redundant components are eliminated and substantial cost savings are realized.

The present invention also provides important advantages with respect to sampling and monitoring capabilities. The integrated apparatus of the invention includes computer control means for automatically calculating fluid condition(s) such as pH level, and for controlling sampling operations on the basis of time and/or fluid condition(s). For example, the apparatus may be instructed by the user to begin a program of sample collection when actual pH falls outside a pre-set acceptable range. The apparatus also stores sample collection and fluid condition(s) data, with access thereto being had either via an alphanumeric display of the apparatus or a portable pocket-sized unit for retrieving and transferring the data to a remote output device such as a conventional printer and/or computer. The invention thus provides convenient means for obtaining a hard copy of the data; storing the data in a remote computer data base; or manipulating the data for statistical analyses, spreadsheeting or the like by a conventional computer provided with a suitable software program.

SUMMARY OF THE INVENTION

The present invention provides an apparatus for automatically monitoring a condition of a fluid, and collecting samples of said fluid on the basis of at least one predetermined parameter. The apparatus comprises a fluid sampling assembly, a fluid condition monitoring assembly, and a computer control means integrally combined substantially within a unitary case. The sampling assembly includes a sample intake conduit adapted to extend into contact with the fluid to be sampled. The fluid condition monitoring assembly includes a sensor selectively connected thereto for detecting at least one variable related to the fluid condition, and outputting a signal proportional thereto. The fluid condition monitoring assembly further includes means for processing signals from the sensor for input to the computer control means. The computer control means is programmed to calculate a value or level of the fluid condition on the basis of processed signals from the fluid condition monitoring assembly, and to automatically control sampling operation of the sampling assembly on the basis of at least one predetermined parameter.

In a preferred embodiment, the at least one predetermined parameter upon which sampling operation of the sampling assembly is based comprises a predetermined time interval and/or at least one predetermined level of the fluid condition being monitored. Such parameter(s) are selected by the user. Further, the computer control means is programmed to automatically collect and store data relating to sampling and monitoring operations of the apparatus, and to provide for calibration of the sensor including prompting the user to perform various calibration steps.

In the various described embodiments, the fluid condition monitored by the apparatus comprises either pH, oxidation reduction potential, activity of a specific ion other than hydrogen, solution conductivity (or resistivity), turbidity and dissolved oxygen. Modifications for monitoring different fluid conditions include employing a different sensor, modifying the interfacing electronics between the sensor and the computer means, and modifying portions of the programming of the computer means. In each embodiment, predetermined levels of the particular fluid condition monitored may be selected by the user to serve as the basis for initiating the sampling program.

Also in accordance with a preferred embodiment, the computer control means is adapted to collect and store fluid condition data and data relating to operation of the sampling operation data. At the user's request, the stored data may be displayed on an alphanumeric screen of the apparatus, or may be selectively transferred by means of a portable data transfer unit to an external output device from which a hard copy of the data may be obtained.

The invention also provides a method for automatically monitoring a condition of fluid in a channel and collecting samples from the channel on the basis of time and/or at least one predetermined level of the fluid condition. The method includes the steps of: connecting a sensor to a fluid condition monitoring assembly for detecting a variable related to the fluid condition; connecting sample intake means to an inlet of a sampling assembly; mounting the sensor in a detecting position relative to the fluid channel; lowering a lower intake end of the sample intake means into the fluid in the channel; positioning an integral operating unit, including the fluid condition monitoring assembly, the sampling assembly and a computer control means all mounted in a unitary case, in an operable position; and operating the computer control means to calculate the level of the fluid condition in the channel on the basis of signals received from the fluid condition monitoring assembly, automatically control sampling operation of the sampling assembly on the basis of predetermined time intervals, flow intervals, and/or predetermined values of the fluid condition, and automatically collect and store fluid condition data and data relating to operation of the sampling assembly.

As with the apparatus according to the invention, the method according to the invention may be employed for monitoring various different fluid conditions, such as pH, oxidation reduction potential, the activity of a specific ion other than hydrogen, solution conductivity (or resistivity), turbidity or dissolved oxygen.

It is a principal object of the invention to provide a compact unitary apparatus which may be conveniently transported and mounted for use to automatically perform fluid sampling operations and/or to monitor at least one condition of the fluid.

In accordance with a further principal of the invention, the user may instruct the apparatus to perform sampling operations on the basis of predetermined time intervals, flow intervals, and/or on the basis of critical level(s) of the fluid condition being monitored. As such, sampling operations may be triggered to begin during critical times of upset in a process stream, such as when the pH level of the fluid falls outside a predetermined acceptable range.

Another important object of the invention is to provide a compact unitary apparatus wherein a common computer means controlling both fluid sampling and fluid condition monitoring operations is adapted to store sample collection data and fluid condition data for later retrieval by the user.

The above and further objects, details and advantages of the invention will become apparent from the following detailed description, when read in conjunction with the accompanying drawings.

BRIEF DESCRIPTION OF THE DRAWINGS

FIGS. 5a and 5b are a flow chart showing operational sequences of the apparatus according to various user commands.

FIGS. 8a and 8b are a flow chart showing operational sequences of the apparatus according to the second embodiment shown in FIG. 7.

FIGS. 12a and 12b are a flow chart showing operational sequences of the apparatus according to the fourth embodiment shown in FIG. 11.

FIGS. 14a and 14b are a flow chart showing operational sequences of the apparatus according to the fifth embodiment shown in FIG. 13.

DETAILED DESCRIPTION OF PREFERRED EMBODIMENTS

FIGS. 1-5 depict an automatic fluid sampling and monitoring apparatus according to a first embodiment of the invention.

Figure 1:
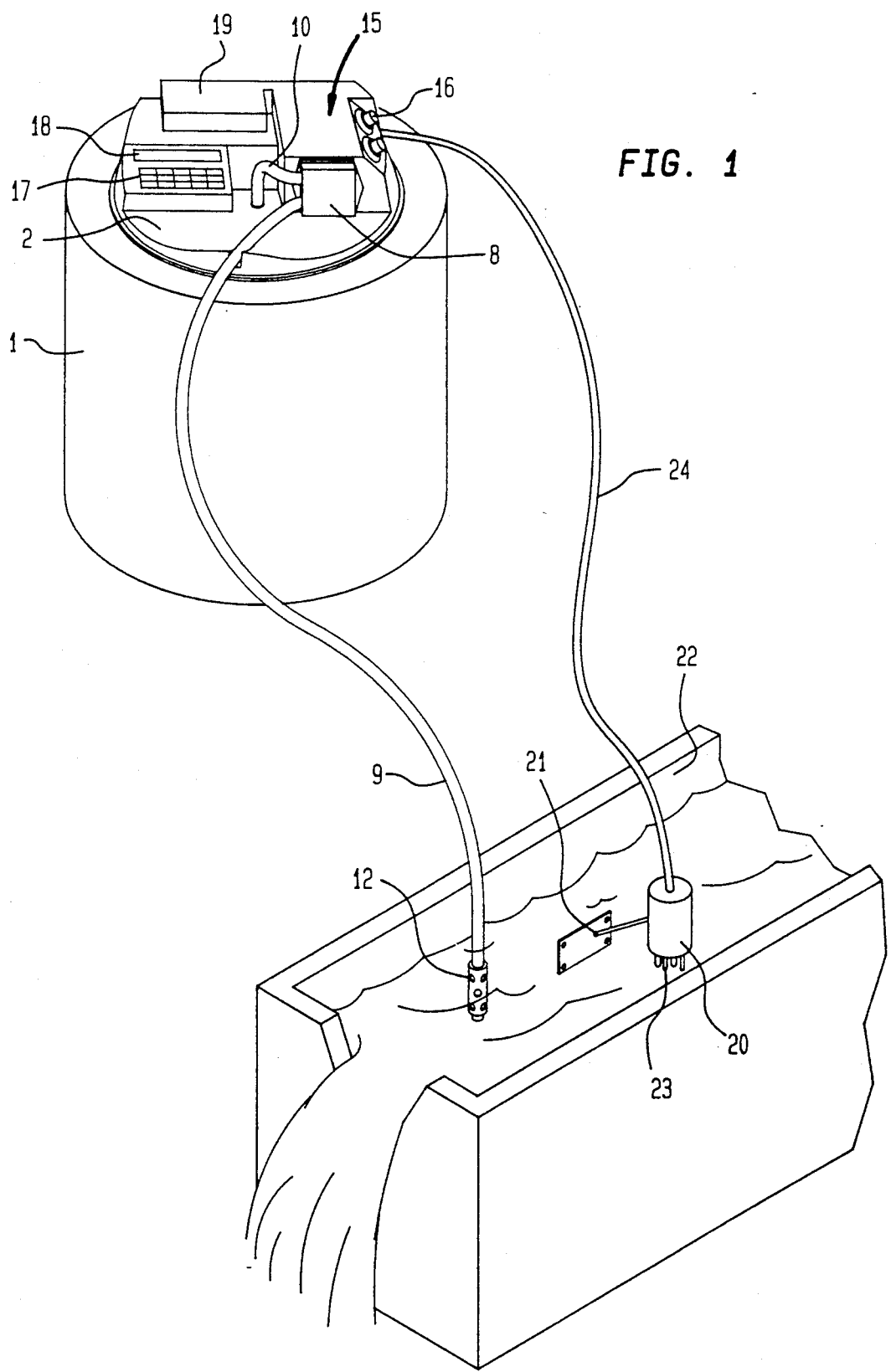
FIG. 1 is a perspective view of an automatic fluid sampling and monitoring apparatus according to a first embodiment of the invention, wherein the fluid condition monitored is pH.
Figure 2:
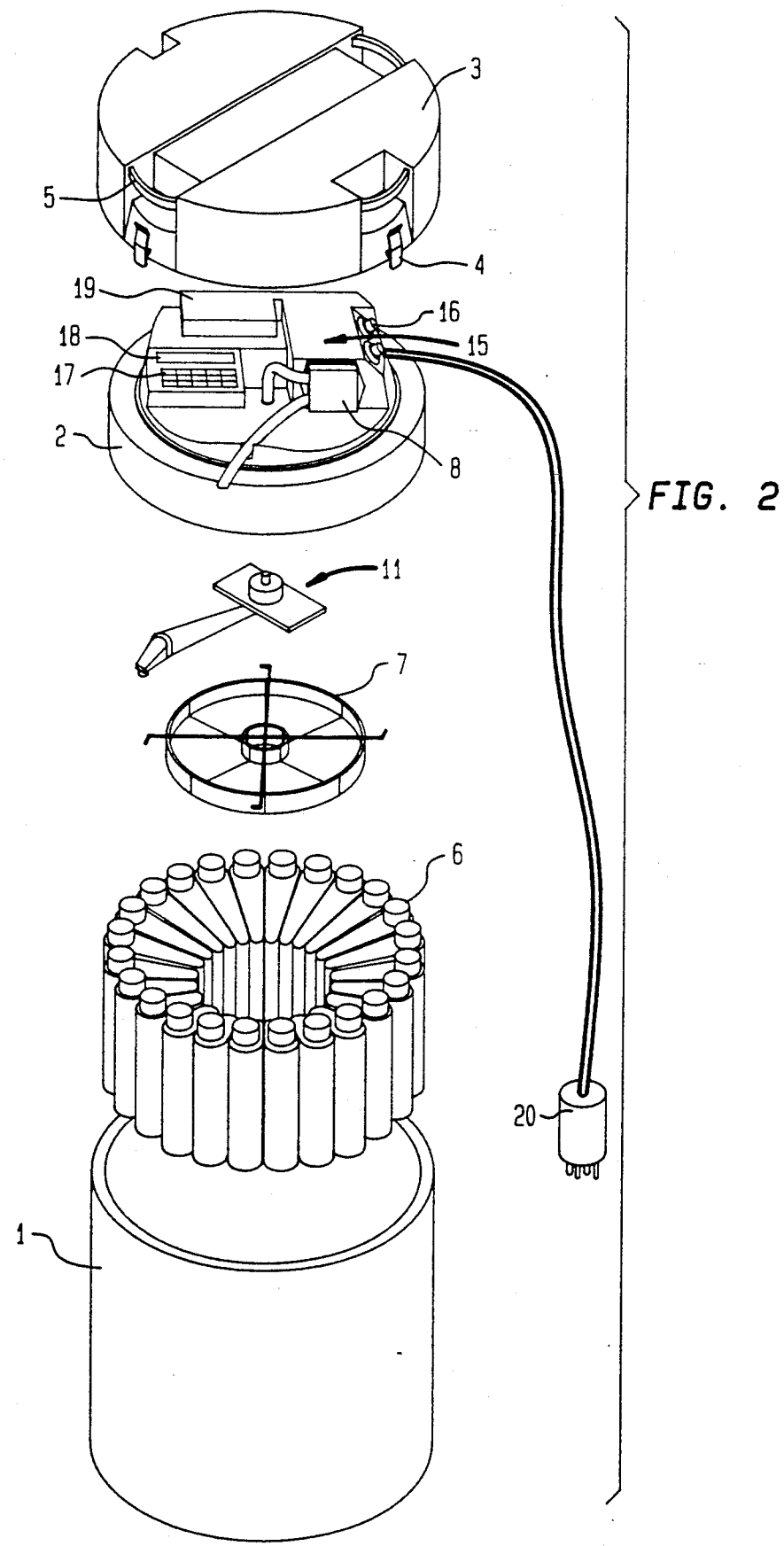
FIG. 2 is a disassembled view of the apparatus according to the first embodiment, including multiple discrete sample containers and a distribution assembly therefor.
Figure 3:
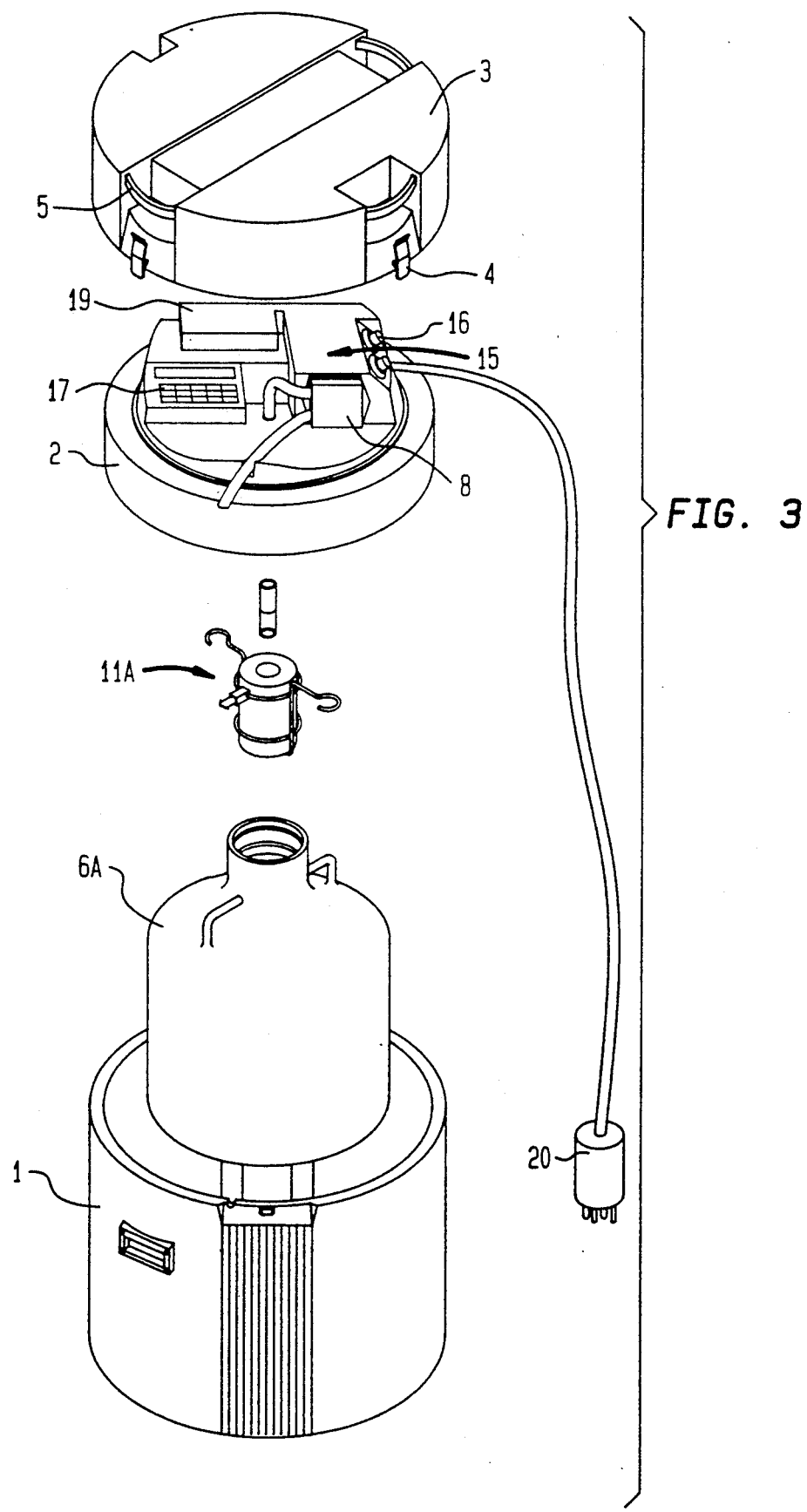
FIG. 3 is a disassembled view of the apparatus of the first embodiment, similar to FIG. 2, except that the multiple sample containers are replaced by a single composite sample container.

As shown in FIGS. 1-3, the apparatus includes a case comprising a lower portion 1 for holding one or more sample containers, an upper component supporting portion 2 and a top cover 3. Each portion of the case is preferably fabricated of a rugged thermoplastic material, such as ABS plastic or molded polyethylene, which is impact resistant and capable of withstanding the stresses of mounting and use in a sewer manhole. The upper component-supporting case portion 2 is adapted to be substantially tightly received in the upper end of lower case portion 1, and the top cover 3 is removably received over upper case portion 2 to protectively enclose the components supported by case portion 2, and to close the case. Top cover 3 is provided with a plurality of fasteners 4 adapted to mate with fastening portions provided at the upper outer surface of lower case portion 1, and handles 5 for ease of transport of the apparatus.

The lower case portion 1 is shown in FIG. 2 as accommodating therein a plurality of sample containers 6. Lower case portion 1 is preferably double-walled with approximately 1" of insulation, for example, to insulate the interior thereof for storing ice to keep sample containers cool. The sample containers 6 are shown in the form of 24 one-liter bottles made of polyethylene or glass, for example. It is to be understood, however, that any number of sample containers ranging from only one to a multiplicity thereof may be employed. Sample containers 6 are supported in a generally circular array.

In a modification of the first embodiment shown in FIG. 3, a single large sample container 6A is accommodated in lower case portion 1 rather than the plurality of containers 6 shown in FIG. 2.

The fluid sampling assembly of the invention may take any desired form of liquid sampler capable of automatic control by a microprocessor to take repeated accurate samples. A sampler having desired characteristics is described in U.S. Pat. No. 4,660,607 issued in 1987 to Griffith et al, the disclosure of which is incorporated herein by reference thereto.

The fluid sampling assembly employed in preferred embodiments of the present invention may be substantially similar to that disclosed in U.S. Pat. No. 4,660,607, and thus only a general description thereof is set forth herein. The assembly includes a reversible, positive displacement pump 8 mounted in casing portion 2 and having the inlet thereof selectively connected to a suitable length of sample intake conduit 9. Provided at the lower intake end of conduit 9 is a weighted strainer member 12 which holds the end of the conduit under water and prevents large objects from entering and blocking the conduit. The upper intake end of conduit 9 is connected to a fluid detection sensor. A second length of conduit 10 is connected to the opposite end of the fluid detection sensor, and through pump 8 to an electro-mechanical distributor mechanism 11 for routing fluid samples to any of the containers 6. A positioning insert 7 is provided between the distributor mechanism 11 and the tray holding sample containers 6. For the single sample container 6A embodiment shown in FIG. 3, the positioning insert 7 and distributor mechanism 11 are replaced by a sample directing member 11A.

The pump 8 is cyclically operated in a reverse purging direction or a forward sample drawing direction depending on signals supplied by processing means incorporated in the computer control means of the present invention, described in detail below. The processing means determines the rate of fluid flow and the time the pump must operate to fill all the tubing plus a desired sample volume, on the basis of signals from a fluid detection sensor disposed upstream of the pump 8, and user programmed data relating to the tubing 9.

It will be understood that pump 8, although described above by way of example as a positive displacement pump, may alternatively comprise any other suitable type of pump, such as a vacuum pressure pump, etc.

As shown in FIGS. 1 and 2, case portion 2 supports other components of the invention in addition to sampler pump 8. The computer control means 15 of the invention is supported by case portion 2, together with a number of external connectors 16 which provide access to computer control means 15. Also supported by case portion 2 is a user-input keypad 17, an alphanumeric display 18 and power supply means 19 which may take the form of a rechargeable battery and/or a power pack for alternatively supplying power to the apparatus from an external AC power source. The aforesaid components supported by case portion 2 are mounted in a watertight manner to protect same from adverse external conditions. Additional protection of such components is afforded by fastening top cover 3 in position, although even without top cover 3 the case with the components mounted therein is submersible, watertight, dust-tight, corrosion resistant and ice resistant (e.g., NEMA 4x, 6).

It will be understood with respect to the following description that the fluid condition analyzing and monitoring features of the invention may alternatively be employed with the above-described fluid sampling assembly alone, or with a combined fluid sampling and flow measuring apparatus such as that described in the present inventors' U.S. patent application Ser. No. 455,981 filed Dec. 22, 1989. The contents of such prior application is incorporated herein by reference thereto. A unitary automatic fluid sampling, flow measuring and fluid condition monitoring apparatus is described in detail below with reference to FIG. 17.

As another alternative, the fluid sampling and monitoring apparatus of the invention may be employed for use in conjunction with a separate external flow meter. Such an arrangement is described in detail below with reference to FIG. 4.

The fluid condition monitoring assembly of the invention, described in detail below, has selectively connected thereto via one of the external connectors 16 a sensing means, or sensor, for detecting a given condition of the fluid in a channel. In the embodiment of FIGS. 1-5, the sensor takes the form of an electrode station 20 including a pH-sensitive electrode, adapted to be submerged in the fluid of a channel to permit electrometric determination of hydrogen ion concentration of the fluid. A multi-conductor cable 24 connects electrode station 20 with one of the external connectors 16, and a suitable mounting bracket 21 may be provided for fixing electrode station 20 in a submerged position.

The electrode station 20 and the end of sample intake conduit 9 may be directly positioned in any fluid source, i.e., either in a gravity fed fluid channel, such as an open flowing sewer passage, or in a pressurized fluid line. By way of example, FIG. 1 shows the electrode station 20 positioned in a fluid flow restricting device 22 in the form of a V-notch weir. Electrode station 20 may also be conveniently positioned in other flow restricting devices such as various types of flumes, weirs or nozzles.

The electrode station or sensor 20 houses the necessary electrodes and temperature sensor for determining hydrogen ion activity of the fluid. Any one of numerous suitable commercially-available sensing devices may be employed as the sensor 20, such as the pH sensor, Model M-11, manufactured by Innovative Sensors, Inc. of Anaheim, Calif. Such sensors typically include a pH electrode, a reference electrode, a temperature sensor, and an optional ground reference electrode.

The pH electrode of the sensor 20 is typically formed of a very thin membrane of a special glass in the form of a small bulb sealed onto a tube of ordinary glass. The glass bulb is filled with an ionic solution, such as potassium chloride, into which is inserted a metal wire such as a silver wire plated with silver chloride. One end of the metal wire is connected to an electrical terminal.

The reference electrode of the sensor 20 typically takes the form of a container filled with potassium chloride solution or similar ionic solution. A metal wire, such as a silver wire plated with silver chloride, is inserted into the solution, with one end thereof connected to an electrical terminal. The boundary between the electrode and the fluid into which it is inserted is made relatively porous so that the ions of the electrode-filling solution may contact or interact with the ions in the process fluid.

A ground reference electrode may also be incorporated in the sensor 20. Although such an electrode is not always necessary, it may be desirable for improving pH signal integrity. The electrode places the electrical ground of the sampling and monitoring apparatus in electrical contact with the process stream, and improves pH signal integrity by limiting the absolute magnitude of the pH and reference electrode signals as measured by the signal conditioning electronics of the invention, described below.

A temperature sensor 23 is arranged together with the three electrodes of the sensor 20 as shown in FIG. 1. The temperature of the fluid source must be known in order to determine pH, and any one of a variety of types of known temperature sensors typically used in pH measuring applications may be employed. For example, semiconductor type sensors may be employed which produce an electrical voltage or current output. Resistance type sensors may also be employed, such as thermistors or resistance temperature detectors (RTD's) which present a temperature-dependent electrical resistance at the terminals thereof.

Voltage and resistance signals from which corresponding pH and temperature may be calculated are conveyed, via multiconductor cable 24, from sensor 20 to the fluid condition monitoring assembly and the computer control means of the invention as described below.

The computer control means and fluid condition monitoring assembly according to the first embodiment of the invention will be described in detail with reference to FIGS. 4 and 5. The boxes labelled "A/D (Analog to Digital) Converter", "Input Selector (Analog Switch)", "Signal Conditioning Electronics (Temperature Sensor)" and "Signal Conditioning Electronics (pH Electrodes)" shown to the right of the dashed line in FIG. 4 essentially comprise the fluid condition monitoring assembly according to the invention, to which the sensor or electrode station 20 is selectively connected.

Together, the A/D converter, input selector and signal conditioning electronics define means for interfacing the computer control means of the invention to the electrode station 20. More specifically, the interface means includes electronic circuitry, with amplifiers, an analog to digital converter, and an analog switch, provided on a single board which is integrally connected with the computer control means.

The signal conditioning electronics of the interface means include both temperature signal conditioning electronics and pH signal conditioning electronics. The temperature signal conditioning electronics convert the resistance, current or voltage from the temperature sensor 23 to a voltage signal of suitable amplitude for the A/D converter. The pH signal conditioning electronics subtract the difference between the voltage output from the pH electrode and the reference electrode, and amplifies the result to a level suitable for the A/D converter. This circuit also presents the pH electrode with an impedance on the order of 1,000,000 megohms ($10^{12}$ ohms). The voltage output of the pH electrode is an accurate indicator of pH only when driving an extremely high impedance load due to the glass construction of the electrode.

The interface means also includes the input selector (analog switch) and the A/D converter. Because two separate signals must be measured in order to determine pH, i.e., the electrode output and temperature, an analog switching device or input selector is provided so as to present one signal at a time to the A/D converter. The A/D converter translates the voltage output from either the temperature signal conditioning electronics or the pH signal conditioning electronics to a binary number which may then be processed by the microprocessor of the computer means according to the invention. A minimum of twelve bits of resolution is required for accurate pH and temperature measurement.

Figure 4:
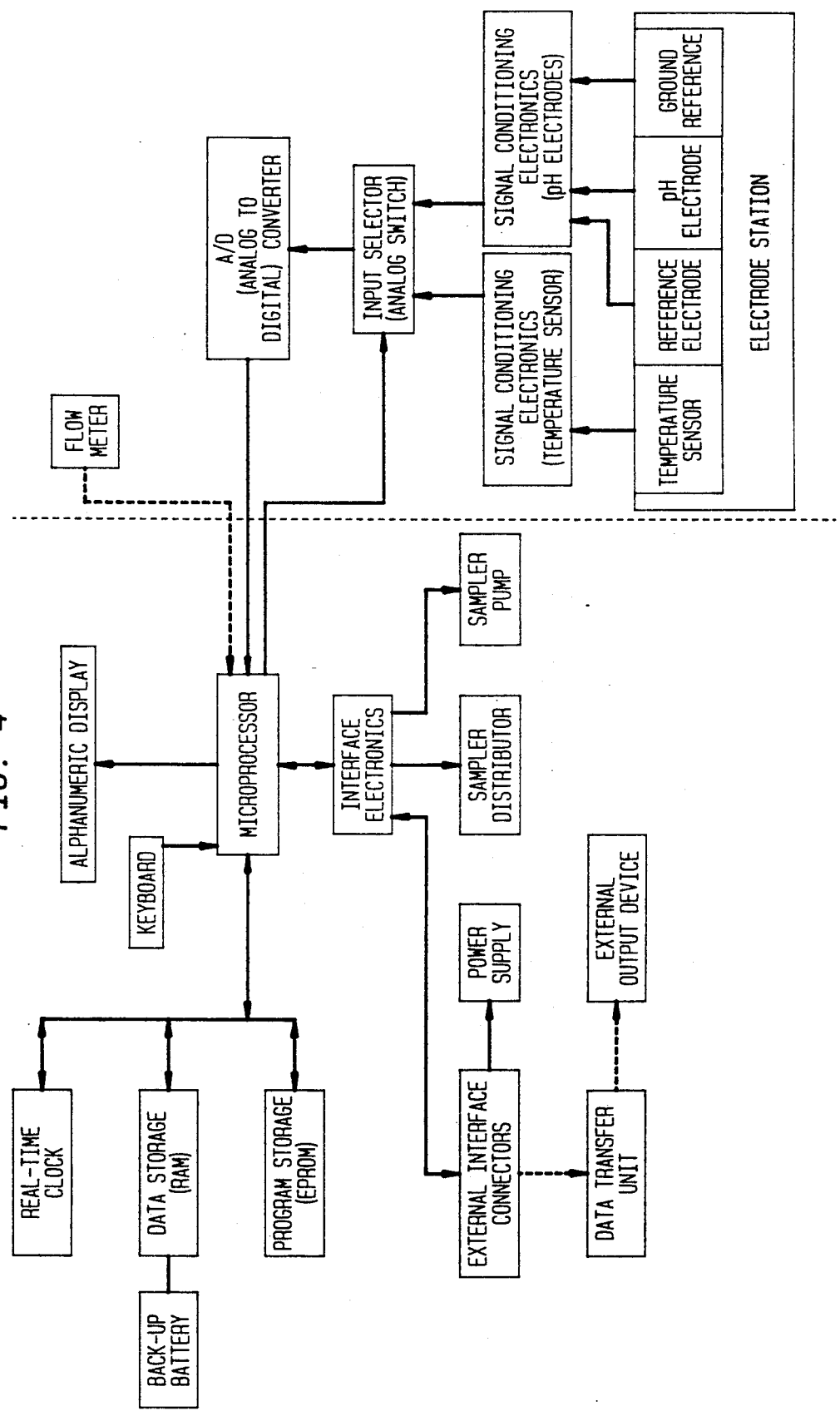
FIG. 4 is a block diagram of the various components of the first embodiment of the invention as controlled by the computer control means, and including an optional external flow meter.

As shown to the left of the dashed line in FIG. 4, the apparatus according to the invention includes a microprocessor which performs all mathematical and control functions required to operate the apparatus, a keyboard (keypad 17 in FIG. 1) comprising the interface to the user allowing the user to program the apparatus and monitor its operation, and a real-time clock. The real-time clock provides the microprocessor with access to current time and date information, so that events occurring during program execution may be recorded with corresponding time and date of occurrence.

As described below, the microprocessor according to the invention includes both program storage memory and data storage memory.

Program Storage Memory

The program storage memory is preferably provided in the form of pre-installed firmware in read-only memory, such as programmed EPROM chips, which control operation of the microprocessor.

The program storage memory (EPROM) of the microprocessor according to the invention implements all of the functions required to operate the sampler pump and distributor, operate the alphanumeric display and keypad, store and retrieve data obtained during execution of a sampling program, and read and process data from the pH electrode station 20.

The program storage memory (EPROM) of the microprocessor includes the following programming, each of which will be described in detail:
Interface Programming;
Sampling Assembly Programming;
pH Analyzer Programming;
pH and Temperature Compensation Equations; and
Floating Point Math Algorithms.

The Interface Programming allows the microprocessor to control the user input keypad 17, alphanumeric display 18, the real-time clock (FIG. 4), and the interface and signal conditioning electronics used by the sampling programming to access the pump and distributor.

The Sampling Assembly Programming allows the microprocessor to control the sampling assembly by implementing user-programmed parameters stored in the data storage memory. The sampling assembly programming includes algorithms using real time, elapsed time, and fluid condition information to collect fluid samples using the sampler pump and the distributor mechanism. Operation of this programming is controlled by user-programmed parameters, described below with reference to the data storage memory.

The pH Analyzer Programming comprises firmware which allows the microprocessor to calculate the pH level on the basis of processed signals received from the fluid condition monitoring assembly and to record calculated data. This programming allows for calibration of the pH electrode, the reference electrode, temperature sensor of the sensing device 20, and permits selection of the time interval for recording pH and temperature data.

The pH and Temperature Compensation Equations include a version of the Nernst equation which describes the voltage output from the combination of the pH electrode and the reference electrode for a given solution pH and temperature. Also included is the output signal vs. temperature characteristic for the temperature sensor.

The Floating Point Math Algorithms comprises programming which allows the microprocessor to perform high precision mathematical operations required to accurately calculate temperature and pH from the raw signals received from the pH and temperature signal conditioning electronics. Included are algorithms for performing addition, substraction, multiplication and division to an equivalent precision of over four significant figures.

Data Storage Memory

Having described the various types of programming provided in the program storage memory (EPROM) of the microprocessor, the data storage memory of the microprocessor will now be described with reference to FIGS. 4 and 5.

The data storage memory is preferably provided in the form of random access memory (RAM) which stores specific details of operation set by the user and records fluid condition and sampling data as described in detail below. The data storage memory (RAM) is backed-up by its own battery, e.g., a lithium battery, so that data will remain stored therein even when the overall power source of the apparatus is turned off. The stored data will thus remain available until a new sampling cycle is started.

The sampling program parameters to be input by the user via keypad 17 and stored in RAM include: program start and stop criteria, time and/or flow interval between samples, pH level(s) for initiating the sampler program, size of the sample, container for sample storage, and rinse and fault conditions for intake conduit 9. These parameters are set out in the leftmost "User Command" column in FIG. 5, under "Specify Sampler Program". The invention contemplates that the microprocessor be programmed to sequentially prompt the user (via display 18) to enter these and other desired parameters via keypad 17.

Figure 5B:
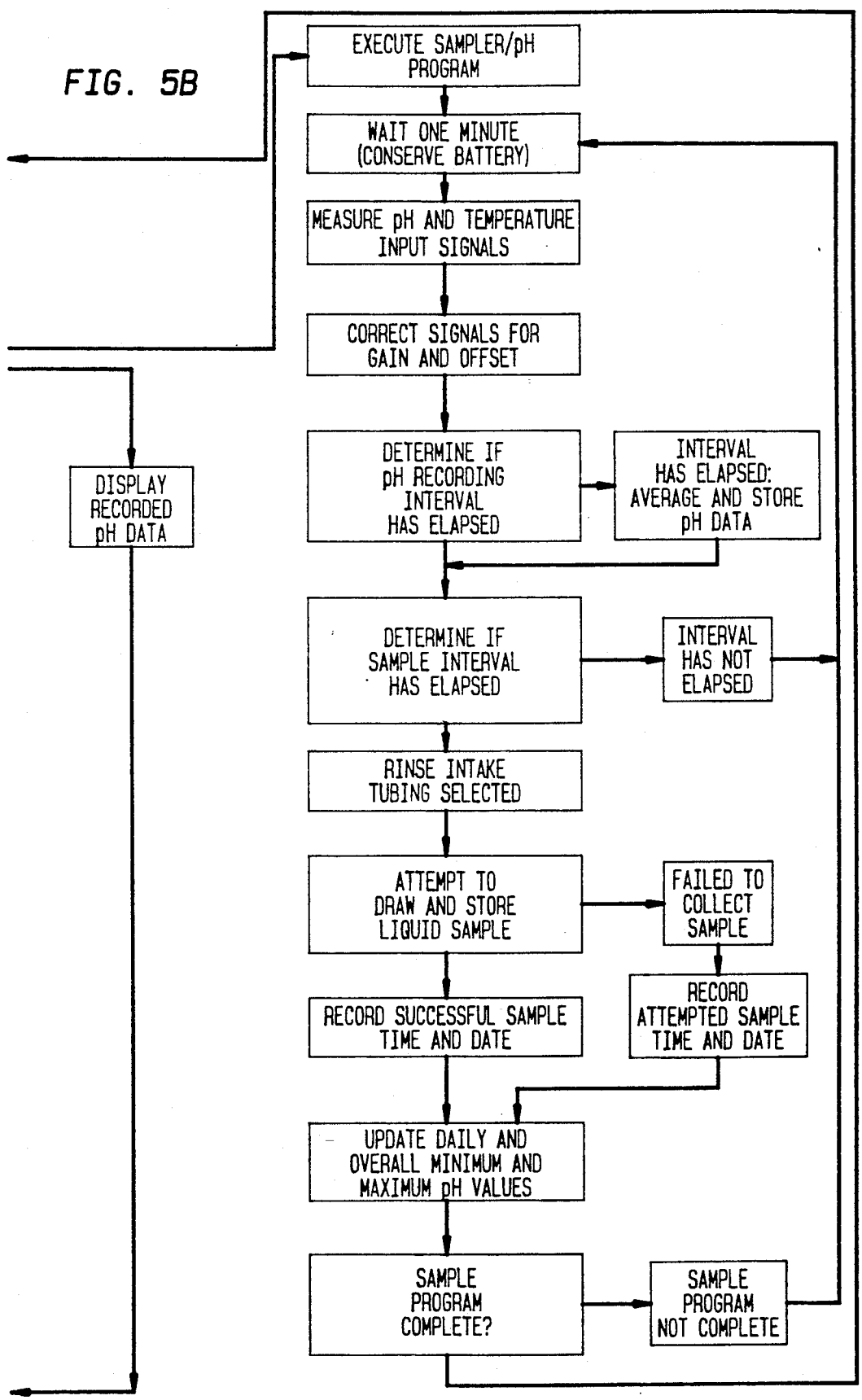

As shown in FIG. 5, one of the sampling program parameters which the user is prompted to input is "Set pH Level(s) to Initiate Sampler Program". The pH level(s) which the user inputs in response to such prompt is stored in RAM along with other user inputs, and provides the unique capability of instructing the apparatus to initiate sample collection on the basis of predetermined pH level(s) as described in greater detail below.

The pH analyzing program parameters to be input by the user via keypad 17 and stored in RAM include: calibration constants for the pH electrode and reference electrode combination, and for the temperature sensor, and time interval for recording pH information.

The microprocessor is programmed such that data will be collected during execution of a fluid sampling program, and will be stored in RAM. Such data includes all programmed entries, the time data of each collected sample, data relating to any failed attempts to collect fluid samples, volume collected, volume remaining, bottle number, and time remaining until the next sample. The pH and temperature data measured by the apparatus is also stored in RAM.

In operation, the user first commands the apparatus, via keypad 17, to implement the "specify sampler program" sequence (leftmost column in FIG. 5). On receipt of this command the apparatus sequentially prompts the user, via alphanumeric display 18, to supply the details of the sampler program which is to be run. As the prompts sequentially appear on display 18, the user's responses are input through keypad 17. The most important information thus input by the user includes: time and date for the program to start and stop; number and size of fluid samples to be collected; time interval and/or quantity of fluid to pass the sampler between collected samples, and pH interval or other external input signal used to initiate and stop collection of a fluid sample.

As depicted in the second column from the left in FIG. 5, the user also commands the apparatus via keypad 17 to implement the "specify pH analyzer operation". On receipt of this command the user is prompted to input the time interval at which the measured pH level is to be recorded. The user is also offered the opportunity to perform a standardization or calibration operation on electrode station 20, described in detail below.

Sampling, Analyzing and Monitoring Operations

When the user commands the apparatus via keypad 17 to "Execute Sampler/pH Program" (right-hand side of FIG. 5), sampling and pH monitoring operations proceed, without further instruction from the user, to collect fluid samples and record pH levels according to program parameters previously entered by the user.

Analysis and monitoring of pH levels by the apparatus according to the invention is performed as follows.

The "pH" signal output from electrode station 20 is taken as the difference in electrical voltage output between the pH and reference electrodes. The Nernst equation describes this voltage signal as a function of solution pH and temperature. The Nernst equation, in generalized form for measuring the activity of any ion, may be stated as follows:

$$E = E_x + 2.3[R \cdot Tk/(n \cdot F)] \cdot \log(Ai) \quad (1)$$

where
E = Voltage difference between the ion-selective (e.g., pH) electrode and the reference electrode
R = Gas Constant of Ideal Gas Law (8.31 J/mol Deg K)
F = Faraday constant ($9.65 \cdot 10^4$ C/mol)
n = Charge on the ion
Tk = Temperature in degrees Kelvin
Ai = Activity of the ion
$E_x$ = Constant determined by the construction and filling solution of the electrodes In the case of pH measurement, it is the hydrogen ion (H+) which is sensed, so that n = 1. pH is defined as the negative base 10 logarithm of the activity of the hydrogen ion. Thus:

$$pH = -\log(H+) \quad (2)$$

The Nernst equation may then be written for pH as follows:

$$E = E_x - 2.3[R \cdot Tk/(n \cdot F)] \cdot pH \quad (3)$$

Or, replacing the known constants with their respective values:

$$E = E_x - 0.198 \cdot Tk \cdot pH \quad (4)$$

Where the electrical output, E, is in millivolts, the Nernst equation term:

$$2.3[R \cdot Tk/(n \cdot F)] \quad (5)$$

is referred to as the electrode "gain" or "Nernst Constant". This value, according to the Nernst equation, is equal to 59.15 millivolts at Tk = 25° C. In actual applications, however, this value is seldom achieved. Electrode gain values typically range from 45 millivolts to 58 millivolts, and generally decreases with the age of the electrode pair.

Manufacturers of pH electrodes typically design their electrode chemistries to achieve an $E_x$ which results in:

$$E = 0 \text{ millivolts (approximately)} \quad (6)$$

for all temperatures and pH = 7.00.

The pH at which E is uniformly zero is referred to as the "Isopotential Point". Among commercially produced electrodes, however, the Isopotential Point will deviate from the 7.00 pH design value by as much as ±0.5 pH for a given electrode pair. The Nernst equation then becomes, for practical applications:

$$E = -G \cdot Tk \cdot (pH - K)$$

where
K = Isopotential Point or pH Offset
G = pH Gain

The pH gain and offset constants must be determined during an electrode calibration process, referred to in the case of pH calibration as "standardization."

The voltage output from the pH electrode set including the pH electrode and the reference electrode cannot generally be determined simply by virtue of its construction. If two different electrode sets were to be exposed to the same liquid, the electrical output from them would generally be different, even if the electrodes were manufactured at the same time by the same process. Further, the output from a given electrode set will typically change during the useful life of the electrodes. The only accurate way of calibrating the pH electrode set is by a process known as standardization.

In a typical standardization process, the electrode set to be standardized is exposed to a liquid of known temperature and pH, referred to as a buffer solution, and the resulting output voltage (E) from the electrode set is recorded. The electrode set is then exposed to a second buffer solution of a different known pH value, and the output voltage (E) is again recorded. The recorded pH, output voltage and temperature data is then applied to the Nernst equation (7), which is solved for K and G as a set of two equations with two unknowns:

$$G = (E_2/Tk_2 - E_1/Tk_1)/(pH_1 - pH_2) \quad (8)$$

$$K = pH_1 + E_1/(G \cdot Tk_1) \qquad (9)$$

where $Tk_1$ = Temperature of first buffer solution in degrees Kelvin
$pH_1$ = pH of first buffer solution at temperature $Tk_1$
$E_1$ = Electrode output voltage for first buffer solution
$Tk_2$ = Temperature of second buffer solution in degrees Kelvin
$pH_2$ = pH of second buffer solution at temperature $Tk_2$
$E_2$ = Electrode output voltage for second buffer solution.

With K and G known for a given electrode set, the electrode output voltage (E) along with the output of a suitable temperature transducer may be applied to the Nernst equation (7) to determine the pH of an unknown fluid. The values of K and G will generally change with time and exposure to various chemicals in the process stream. The standardization process must thus be repeated periodically to retain accuracy.

As described above, the opportunity to perform a standardization operation of the electrode station 20 is offered to the user when the "specify pH analyzer operation" command is given via keypad 17. The sequential prompts appearing on display 18 during standardization are shown in FIG. 5. As also described above, programming for implementing the standardization procedure and performing necessary calculations is provided in the program storage memory (EPROM) of the microprocessor of the apparatus.

Because the sampling and pH monitoring capabilities of the apparatus are controlled by a common computer means, the apparatus provides the unique capability of permitting the user to instruct the apparatus to initiate sample collection on the basis of predetermined pH level(s) as mentioned above. Should an out-of-tolerance condition be detected during pH monitoring operations, i.e., if pH level falls outside a predetermined acceptable range set by the user, or above or below a given level set by the user, the apparatus will automatically initiate sample collection. By thus triggering sample collection on the basis of pH level(s), the apparatus provides the unique capability of ensuring that samples are collected at critical times of upset in the process stream.

In addition to sample collection triggered by critical pH level(s), the apparatus is also capable of collecting samples on the basis of time and/or flow intervals as described above. It will be understood that the user is thus provided with a unique range of control over sample collection, and may instruct the apparatus to initiate the sampler program on the basis of any one or more of various desired parameters. As each new sampling cycle is started, the apparatus can be instructed to initiate the sampler program on the basis of time, flow or pH level(s), or to simultaneously use all three parameters for controlling sample collection.

User Access to Stored Data

As depicted in the User Command section of FIG. 5, the user can request (via keypad 17) that the sampler program and/or pH data stored in RAM be displayed on display 18 when desired. The sampler program display permits the user to review the details of the sampler program and pH monitoring operation previously specified by the user. The pH data display provides the user with pH values recorded during the current or most recently completed sampler/pH program. Because the data storage memory comprises battery backed-up RAM, stored sampler program and pH data will remain available for retrieval by the user until a "start" button is pressed to begin a new sampling cycle.

The invention provides an alternative means for retrieving stored sampler program and pH data in the form of a portable data transfer unit, indicated in the lowermost box of FIG. 4. The portable data transfer unit is preferably very compact, i.e., pocket-sized, so that the user can conveniently carry same for selective use. The data transfer unit is provided with its own microprocessor, the memory of which may take the form of CMOS RAM chips powered by a lithium battery (battery backed-up RAM). The unit is also preferably provided with a user-input keypad and an alphanumeric display, and resembles a conventional small pocket calculator in overall appearance.

The data transfer unit is connected via a conventional connector cable (not shown) with one of the connectors 16, which may comprise a conventional 6-pin computer connector jack capable of a watertight connection. The user may then send an electronic data request command from the data transfer unit to the microprocessor of the apparatus, as indicated diagrammatically in the upper left portion of FIG. 5. Upon receipt of such command, the microprocessor of the apparatus retrieves the requested data from its RAM and sends it for storage in the memory of the data transfer unit, via the connector 16.

When it is desired to retrieve the data thus stored in the data transfer unit, the unit is in turn connected, via a standard computer or printer jack for example, to an external output device (FIG. 4) in the form of a conventional printer or computer (e.g., a personal computer). The stored data can be read out directly on a printer to produce a hard copy thereof, with the microprocessor of the data transfer unit itself operating the printer in a known manner. The user is thus able to obtain a complete and accurate hard copy record of the data. Alternatively, the stored data can be transferred to a conventional computer for manipulation using an available software program for statistical analyses, spreadsheeting, etc.; for more permanent storage in a database stored in the computer's memory; and/or for printing by a printer connected to the computer.

Although it may not often be practical, the external connector 16 described above can alternatively be directly linked to a remote computer for direct transfer of the stored data if and when the apparatus itself is transported into close proximity with a computer. However, use of the portable data transfer unit offers a more convenient alternative.

With reference to FIG. 4, there is shown an external flow meter which may optionally be employed in conjunction with the automatic fluid sampling and pH monitoring apparatus described above. It will also be understood that an external flow meter may be used in conjunction with the various alternative embodiments of the invention described in detail below, where the apparatus is designed to monitor fluid conditions other than pH. The external flow meter may comprise any one of a variety of suitable commercially-available flow meters, such as one of the Model 8100 series of flow meters manufactured by American Sigma, Inc. of Middleport, N.Y. The external flow meter may be connected to the apparatus of the invention via one of the external connectors 16, so as to communicate with the computer -control means of the invention and provide the further option of controlling sampling operations on the basis of predetermined flow intervals.

Figure 17:
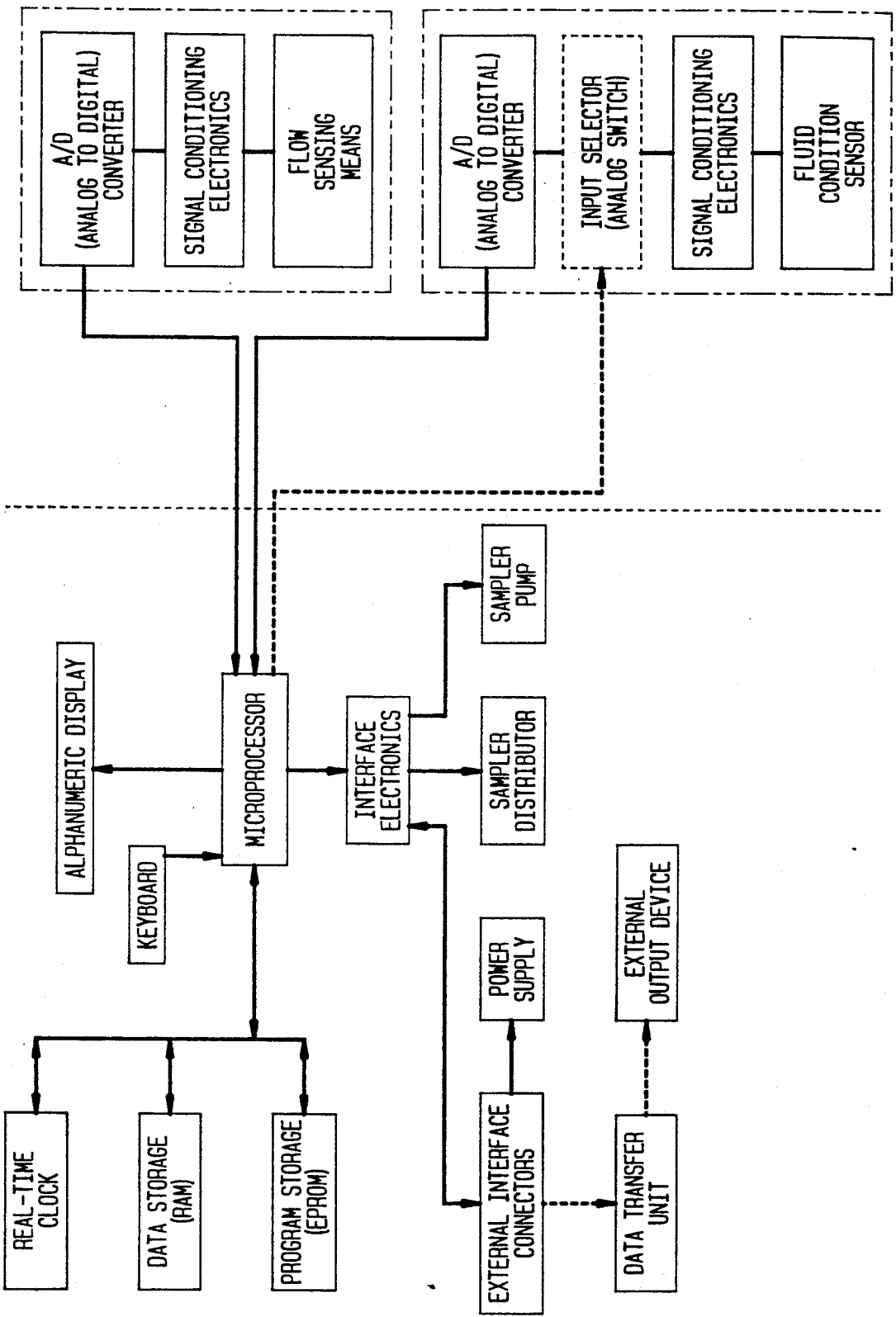
FIG. 17 is a block diagram generally illustrating the automatic fluid sampling and monitoring apparatus of the invention, and incorporating an integral flow measuring assembly.

As shown in FIG. 17, the apparatus according to each of the different monitoring embodiments of the invention may also incorporate its own internal flow measuring assembly, such as disclosed in the present inventors' prior U.S. patent application Ser. No. 455,981 filed Dec. 22, 1989. In FIG. 17, both a flow measuring assembly and a fluid condition monitoring assembly are shown to the right of the dashed line. The apparatus including the computer control means, the sampling assembly, the flow measuring assembly and the fluid condition monitoring assembly defines a compact unitary structure, similar to that described above and shown in FIGS. 1-3.

The flow measuring assembly of FIG. 17 includes a flow sensing means for detecting a variable related to fluid flow and outputting a signal proportional thereto, such as a pressure transducer type sensor, an ultrasonic type sensor, a float type sensor, etc. Interface means including an A/D converter and signal conditioning electronics are provided for processing signals from the flow sensor and inputting same to the computer control means. The program storage memory of the microprocessor is provided with flow measuring assembly programming which allows the microprocessor to calculate the flow rate on the basis of processed signals received from the flow measuring assembly, and to record calculated flow rate data. As shown in the leftmost column of FIG. 5, the user can set the desired flow recording interval as desired. Although not shown, the user is also offered the opportunity to calibrate the flow sensor.

The fluid condition monitoring assembly shown in FIG. 17 may comprise either a pH monitoring assembly as described above, or any one of the alternative monitoring assemblies described below.

The apparatus of FIG. 17, in addition to providing the capability of controlling sampling operations on the basis of time and/or a given fluid condition, provides the capability of automatically controlling sampling operations in proportion to calculated flow rate, i.e., on the basis of flow intervals selected by the user. The user may access stored data relating to the sampler program, flow rate and/or the given fluid condition being monitored by requesting either that it be displayed on alphanumeric display 18 or transmitted electronically to the data transfer unit for subsequent analysis, permanent storage or obtaining a hard copy. Because the sampling assembly, flow measuring assembly and fluid condition monitoring assembly share a common computer control means, a very versatile apparatus having each of the foregoing capabilities may be provided as a compact unitary structure.

ALTERNATIVE EMBODIMENTS

The particular fluid condition monitored by the apparatus according to the invention in conjunction with sample collection is not limited to pH level, and various other fluid conditions may be monitored by the apparatus instead of or in addition to pH level. In various alternative embodiments of the invention described below, the apparatus is modified to monitor other fluid conditions. The foregoing detailed descriptions of the sampling means, computer control means including program and data storage memories, and various other components of the apparatus are equally applicable to the following embodiments. The modifications required to monitor various other fluid conditions will become apparent from the following description, when read in conjunction with FIGS. 6-16.

Figure 6:
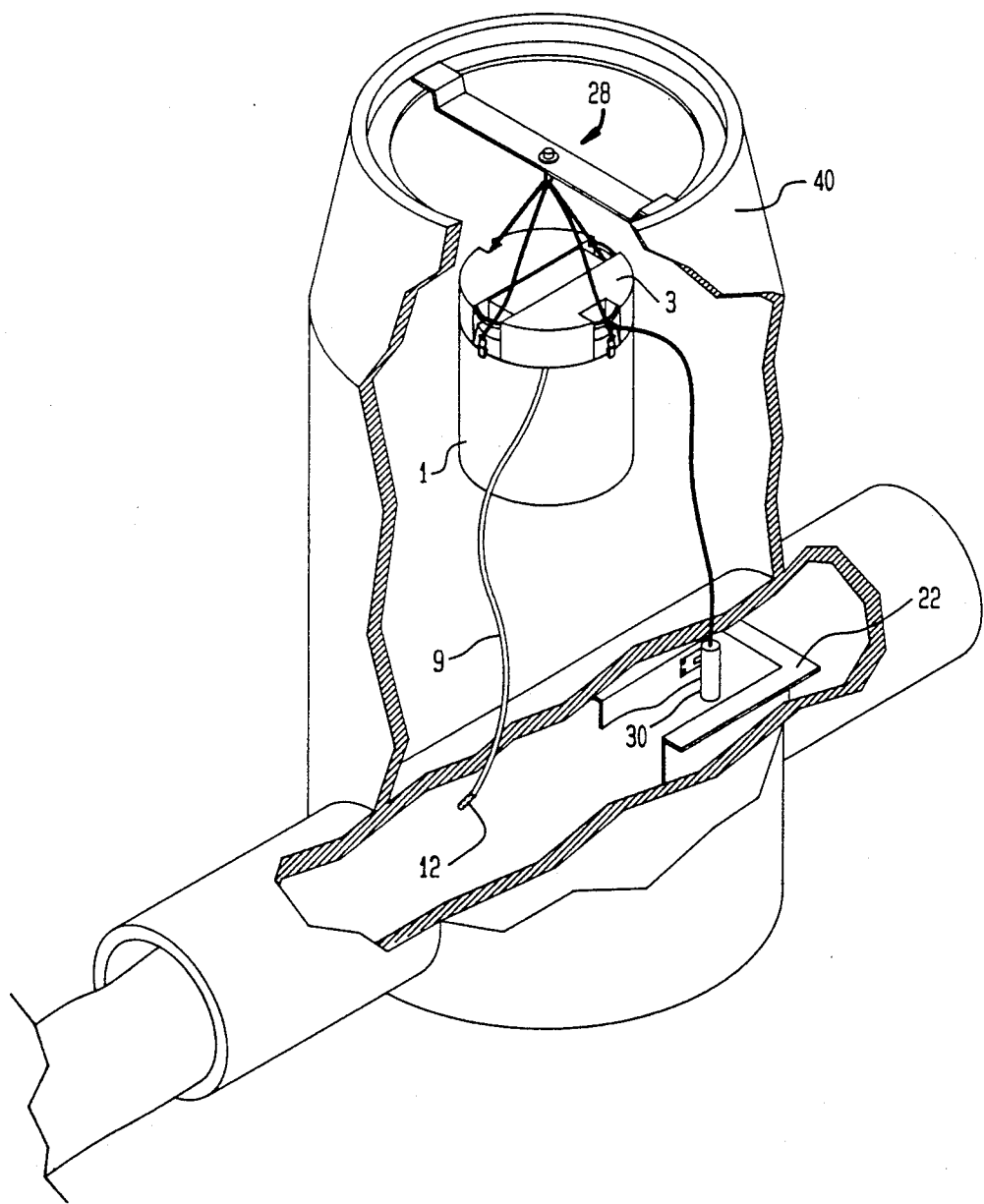
FIG. 6 is a perspective view of the sampling and monitoring apparatus of the invention, shown mounted in an operative position in a sewer manhole.

In FIG. 6, an automatic fluid sampling and monitoring apparatus in accordance with the invention is shown in a mounted position within a sewer manhole 40. It will be understood that the apparatus shown in FIG. 6 represents any one of various embodiments of the invention, including the first embodiment described above. As such, the electrode station 30 shown positioned in the flow restricting device 22 is intended to generally represent any one of various types of electrode stations, such as a pH electrode station as described above or other types of electrode stations as described below, depending upon the particular fluid condition to be monitored by the apparatus. Also shown in FIG. 6 is a suspending means 28 including a cross-bar support extending across the upper end of the manhole and a plurality of lines extending from the support to fastening portions provided on the case of the apparatus. If desired, such fastening portions may comprise portions of fasteners 4 used to fasten cover 3 to lower case portion 1.

The automatic fluid sampling and monitoring apparatus in accordance with other embodiments of the invention, wherein fluid conditions other than or in addition to pH level are monitored by the apparatus, are described below.

1. Oxidation Reduction Potential

Figure 7:
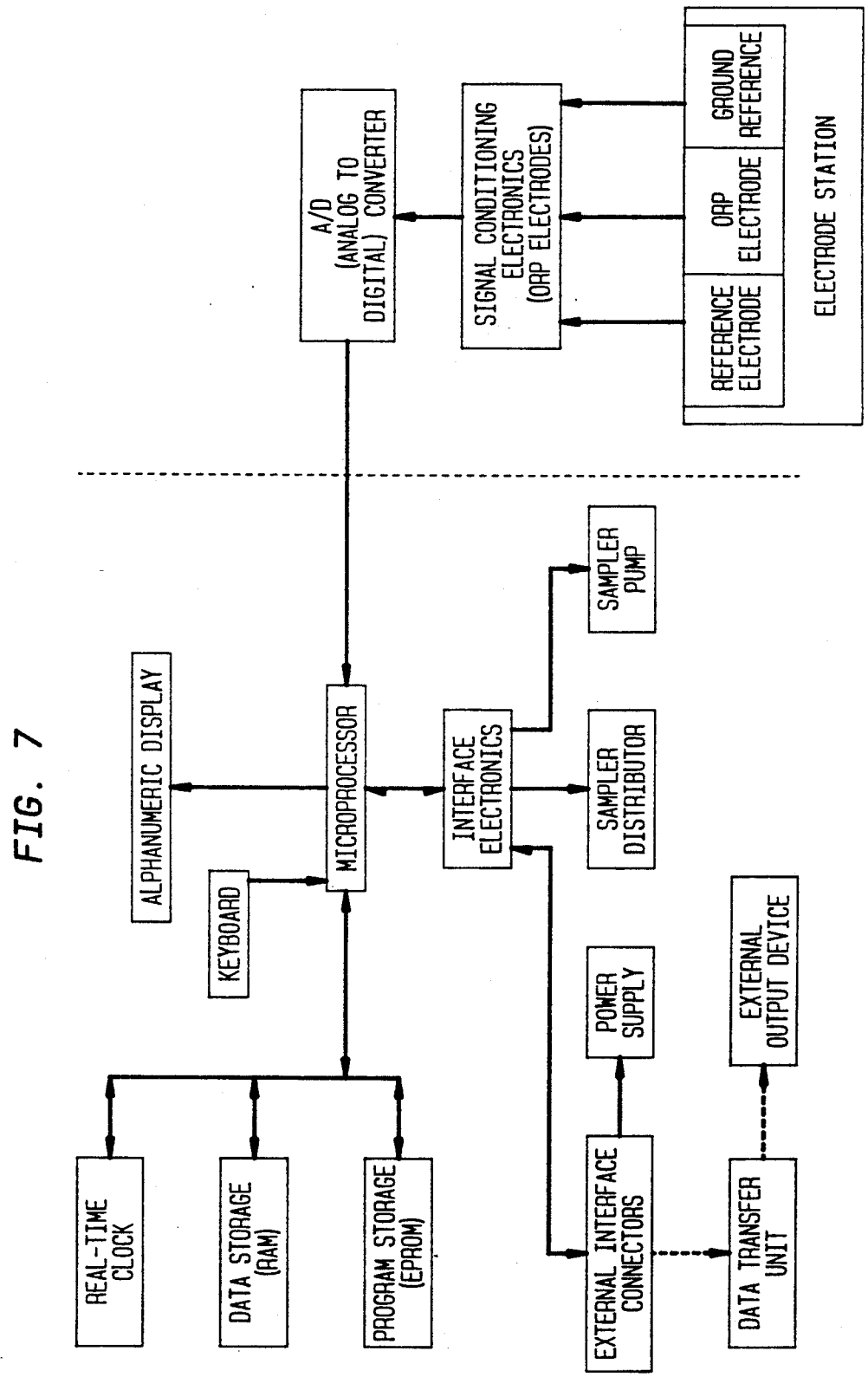
FIG. 7 is a block diagram of the various components of a second embodiment of the invention wherein the fluid condition monitored is oxidation reduction potential.
Figure 8B:
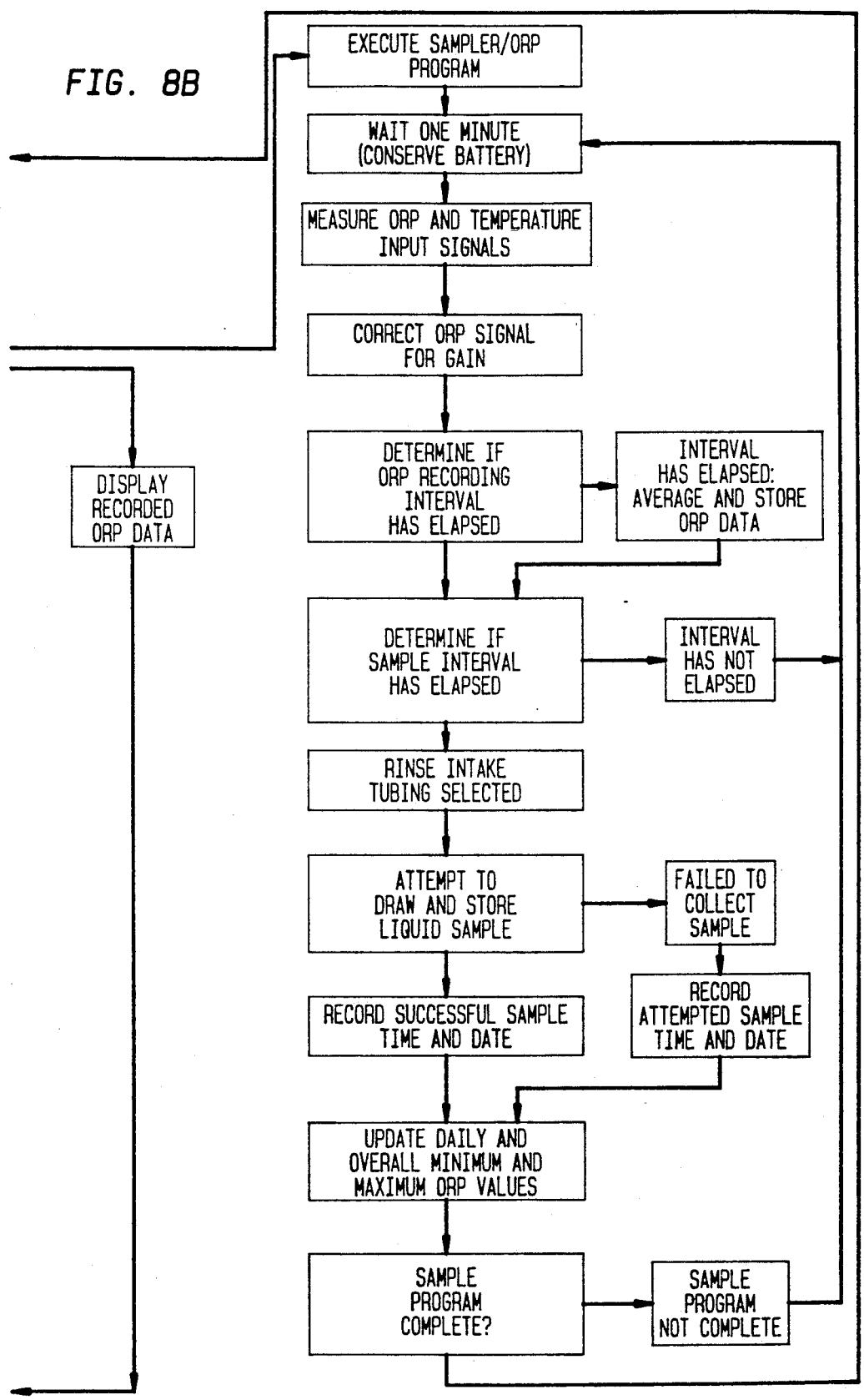

The second embodiment of the invention shown in FIGS. 7 and 8 provides an automatic fluid sampling and oxidation reduction potential monitoring apparatus, i.e., the fluid condition analyzed and monitored by the apparatus is oxidation reduction potential.

In a variety of wastewater-related applications it is necessary to control the oxidation reduction potential ("ORP") of the process stream. Two examples include oxidation of cyanide, and reduction of such plating wastes as chromium. If the control system fails to maintain the correct ORP level, toxic material may remain present in the wastewater stream.

ORP is measured in a manner very similar to pH, so that in this embodiment of the invention the sensor 30 of FIG. 6 takes much the same form as the electrode station 20 described above with respect to the first embodiment of the invention. The principal difference between pH and ORP measurement is that temperature information is not necessary to measure ORP because ORP is simply the potential difference measured between an ORP electrode and a reference electrode (measured in millivolts). The pH sensitive glass electrode described above with respect to electrode station 20 is in this embodiment replaced with a noble metal electrode (typically platinum or gold) which is exposed to the process fluid along with a reference electrode. The reference electrode is of the same type as described above for pH measurement. The voltage difference between the ORP electrode and the reference electrode represents the ORP. The ORP electrode station or sensor, including the reference electrode, the ORP electrode, and a ground electrode, is depicted to the right of the dashed line in FIG. 7.

An example of a commercially available ORP sensor suitable for use with the invention is the Model M-11-ORP sensor manufactured by Innovative Sensors, Inc. of Anaheim, California. It will be understood, however, that any other suitable commercially-available ORP sensor may be employed.

As shown in the block diagram of FIG. 7 and the flow chart of FIG. 8, the apparatus including the computer means is much the same for the second embodiment of the apparatus as it is for the first embodiment described above. The differences can best be understood with reference to the boxes shown to the right of the dashed line in FIG. 7, which comprise the fluid condition monitoring assembly for monitoring ORP according to the second embodiment. In addition to the above noted differences in electrode station or sensor 30, this embodiment of the invention also differs from the first embodiment inasmuch as the temperature sensor and temperature sensor conditioning electronics are not required. The flow chart of FIG. 8 also reflects these differences, inasmuch as temperature calibration and measurement are eliminated, and the input need be calibrated at only one point. As shown in the "calibrate ORP inputs" portion of the FIG. 8 flow chart, a voltage source of known value may be used for calibration rather than the chemical buffer solutions described above for pH calibration, and the user is prompted accordingly.

The ORP monitoring capability of the apparatus of FIGS. 7 and 8 permits the user to verify that an acceptable ORP level is maintained in the wastewater stream. In this embodiment, the program storage memory of the microprocessor is provided with ORP Analyzer Programming in the form of firmware which allows the microprocessor to calculate the ORP level on the basis of processed signals received from the fluid condition monitoring assembly, and to record calculated ORP data. As shown in FIG. 8, the user can set the desired ORP recording interval as desired.

By virtue of the sampling and ORP monitoring capabilities of the apparatus and the common computer means controlling same, the user can instruct the apparatus to initiate the sampler program on the basis of predetermined ORP level(s). As shown in the leftmost column of FIG. 8, the user is prompted to "Set ORP Level(s) to Initiate Sampler Program". The ORP level(s) which the user inputs is stored in RAM along with other user inputs. Should an out-of-tolerance condition be detected during ORP monitoring operations, i.e., if ORP level falls outside a predetermined range set by the user, or above or below a given level set by the user, the apparatus will automatically initiate sample collection. By thus triggering sample collection on the basis of ORP level(s), the apparatus provides the unique capability of ensuring that samples are collected at critical times of upset in the process stream.

As described above with respect to the first embodiment, the apparatus according to the second embodiment of the invention may also be instructed to perform sampling operations on the basis of time and/or fluid flow (see FIG. 8). Also similar to the first embodiment, the ORP monitoring embodiment permits the user to access stored sampler program and/or ORP data stored in RAM by requesting either that the data be displayed on alphanumeric display 18, or that it be transmitted electronically to the data transfer unit for subsequent analysis, permanent storage or obtaining a hard copy (see FIG. 7).

2. Specific Ion

Figure 9:
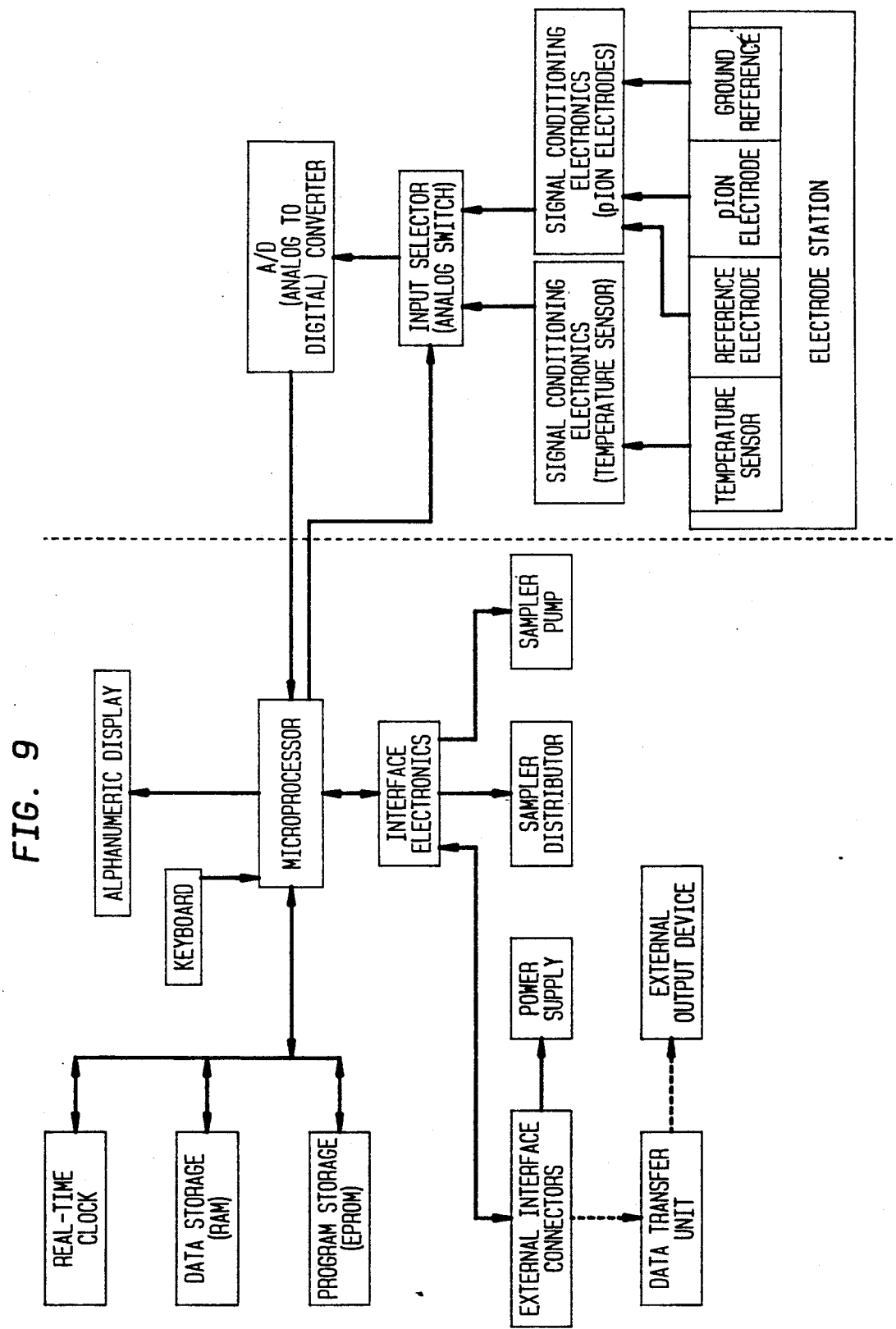
FIG. 9 is a block diagram of the various components of a third embodiment of the invention wherein the fluid condition monitored is the activity of a specific ion other than hydrogen.
Figure 10:
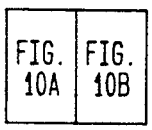
FIGS. 10a and 10b are a flow chart showing operational sequences of the apparatus according to the third embodiment shown in FIG. 9.
Figure 10A:
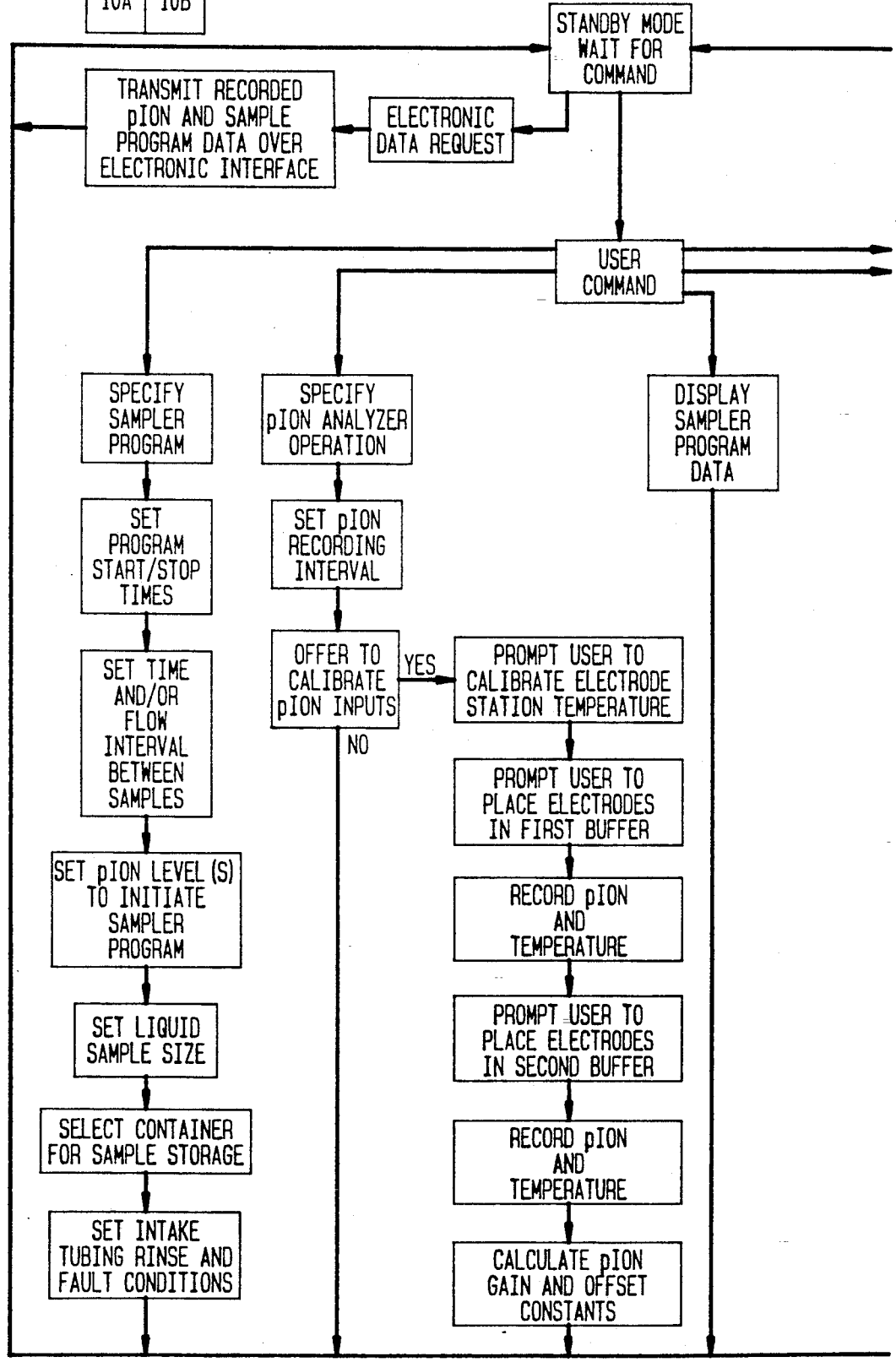
Figure 10B:
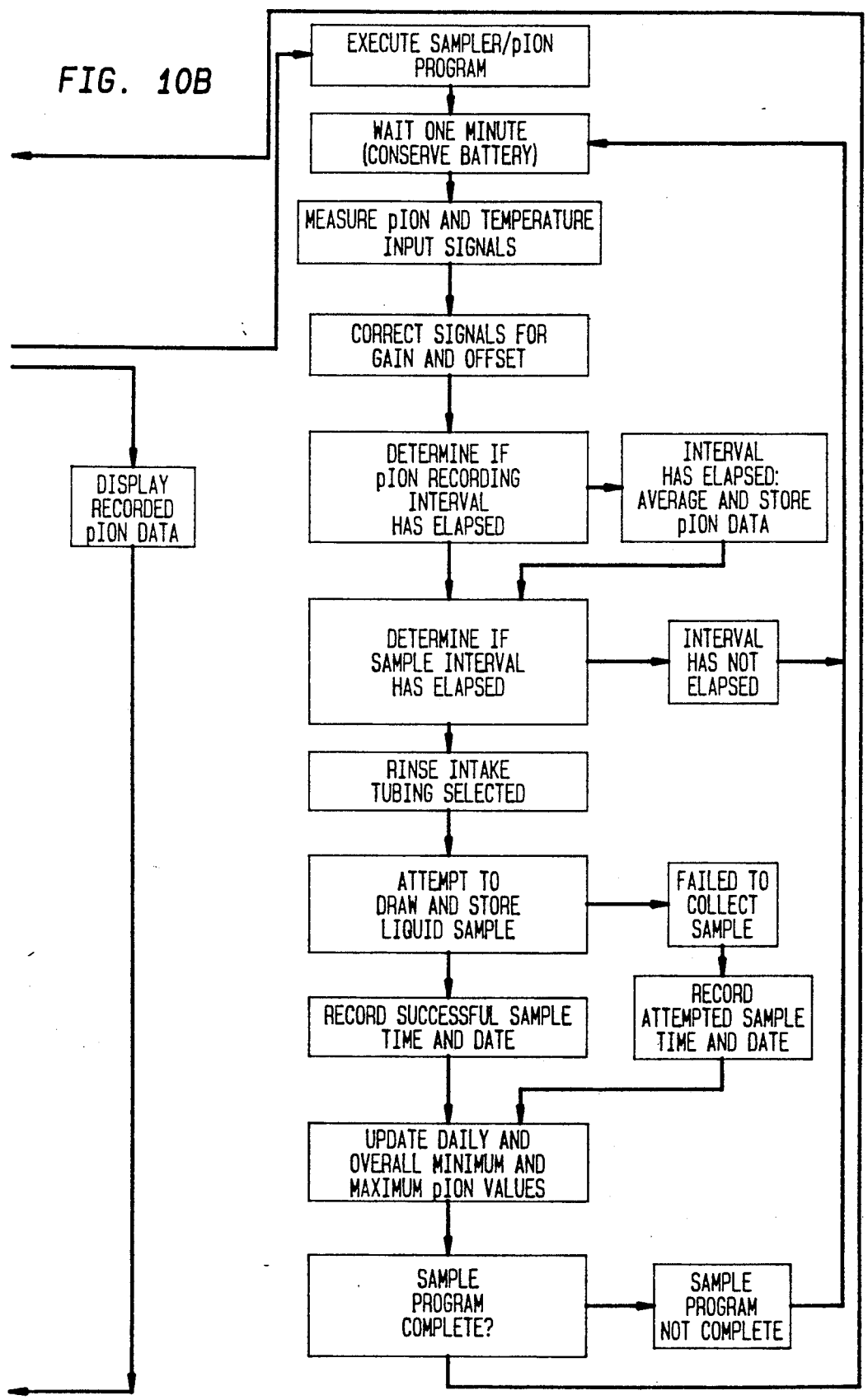

The third embodiment of the invention shown in FIGS. 9 and 10 provides an automatic fluid sampling and specific ion monitoring apparatus, i.e., the fluid condition monitored by the apparatus is the activity of a specific ion other than hydrogen ("pION").

The measurement of pION is nearly identical to that of pH. In this embodiment, the sensor 30 of FIG. 6 is thus substantially the same as the electrode station 20 described above with respect to the first embodiment. The principal difference between the sensors used for pH and pION measurement is that in a pION sensor the pH electrode, made of a glass sensitive to the hydrogen (H+) ion, is replaced with an electrode made of a glass sensitive to some other ion. Common examples of ion specific electrodes which might be used include sodium, bromide, chloride, and cyanide, amongst others. An example of one of the many commercially-available pION sensors suitable for use with the invention is the sodium ion sensor, Model ISE-8765, manufactured by Omega Engineering, Inc. of Stamford, Connecticut.

As shown in the block diagram of FIG. 9 and the flow chart of FIG. 10, the apparatus including the computer means is substantially the same for the third embodiment of the apparatus as it is for the first embodiment described above. In this embodiment, the program storage memory is programmed to calculate pION level on the basis of processed signals from the fluid condition monitoring assembly. As will be understood with reference to the boxes shown to the right of the dashed line in FIG. 9, the fluid condition monitoring assembly for monitoring pION levels according to the third embodiment is substantially the same as that of the first embodiment, except that a pION electrode station is employed. The electronics employed for conditioning the inputs from the electrodes of the pION electrode station are substantially identical to those employed for pH as described above with respect to the first embodiment.

In operation, pION measurements are typically more difficult to perform that pH measurements due to the difficulty of manufacturing an electrode sensitive to a single type of ion (other than pH). To the extent that other types of ion sensitive electrodes are typically subject to more error than pH electrodes, the widespread practical application of generalized pION measurement is more limited than pH measurement. However, pION monitoring does find use in some applications.

The pION monitoring capability of the apparatus of FIGS. 9 and 10 permits the user to verify that an acceptable pION level is maintained in the wastewater stream. As shown in FIG. 10, the user can set the desired pION recording interval as desired.

Similar to the foregoing embodiments, the third embodiment of the invention provides the unique capability of triggering sampling operations on the basis of a given fluid condition, i.e., pION level in this embodiment. The user can instruct the apparatus to initiate the sampler program on the basis of predetermined pION level(s). As shown in the leftmost column of FIG. 10, the user is prompted to "Set pION Level(s) to Initiate Sampler Program", and the pION level(s) which the user inputs is stored in RAM along with other user inputs. Should an out-of-tolerance condition be detected during pION monitoring operations, such as where the level of the ionic compound of interest falls outside a predetermined range set by the user, or above or below a given level set by the user, the apparatus will automatically initiate sample collection. Also similar to the above embodiments, the present embodiment may be instructed to initiate the sampler program on the basis of time and/or fluid flow (see FIG. 10), and the user may access stored sampler program and/or pION data by requesting either that it be displayed on alphanumeric display 18 or transmitted electronically to the data transfer unit for subsequent analysis, permanent storage or obtaining a hard copy (see FIG. 9).

3. Solution Conductivity (or Resistivity)

Figure 11:
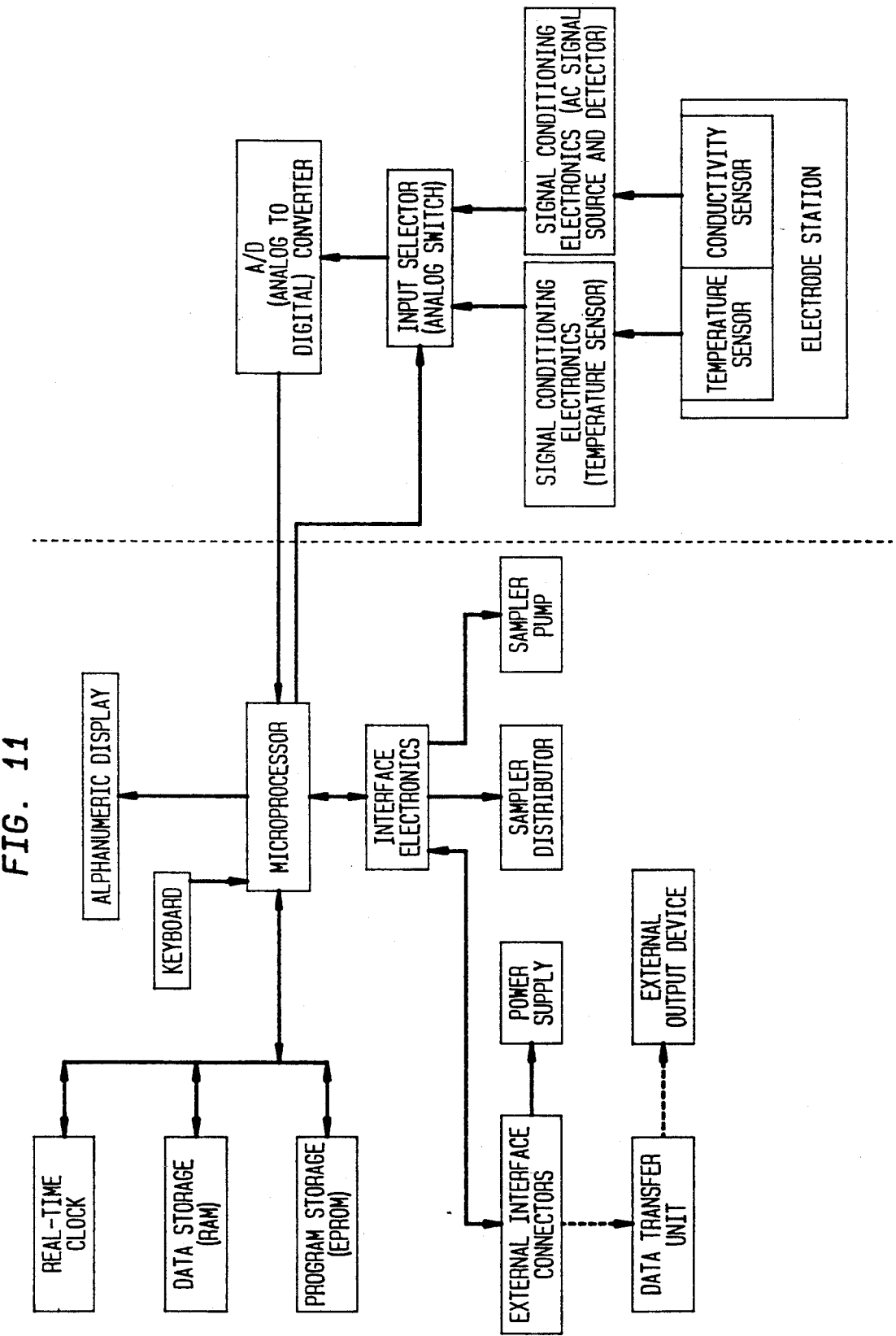
FIG. 11 is a block diagram of the various components of a fourth embodiment of the invention wherein the fluid condition monitored is solution conductivity.
Figure 12B:
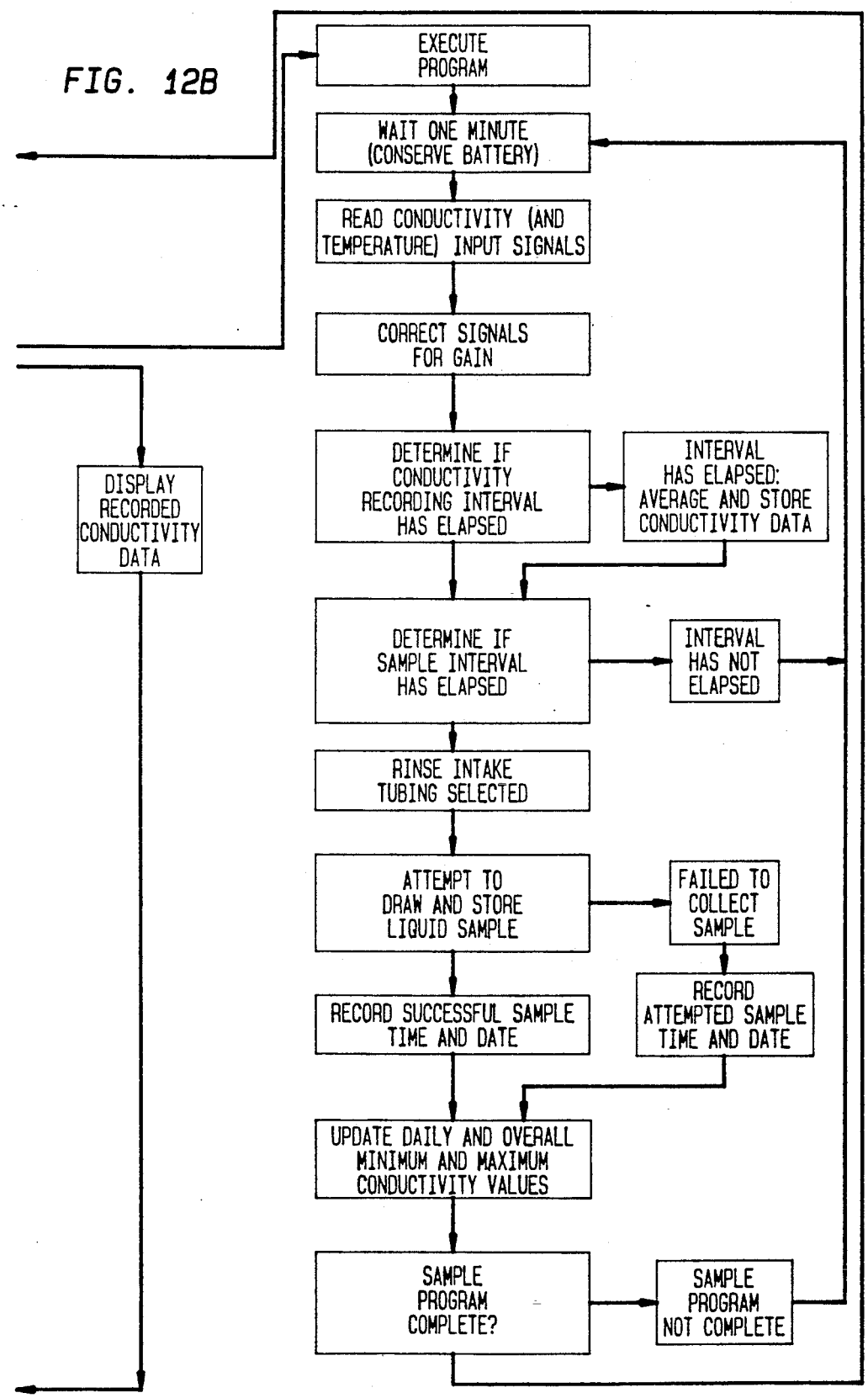

The fourth embodiment of the invention shown in FIGS. 11 and 12 provides an automatic fluid sampling and solution conductivity (or resistivity) monitoring apparatus, i.e., the fluid condition analyzed and monitored by the apparatus is the solution conductivity or its inverse, solution resistivity.

The measurement of solution conductivity is substantially different from that of pH. In this embodiment, the sensor 30 of FIG. 6 thus has a substantially different structure than the pH electrode station. The electronics for interfacing the sensor are also substantially modified in this embodiment, as is the programming in the form of firmware which allows the microprocessor to calculate the solution conductivity on the basis of signals received from the fluid condition monitoring assembly.

Solution conductivity, or its inverse solution resistivity, may be used to measure levels of soluble salts in aqueous solution. The levels of acids and bases, and other substances which change the conductivity of a fluid, may also be monitored by measuring solution conductivity.

The basic structure of a solution conductivity sensor is in the form of a transducer comprising two conductive surfaces or "plates" separated by an insulator, such that the geometry of the surfaces remain fixed relative to each other. An example of one of the many commercially-available conductivity sensors suitable for use with the invention is the conductivity sensor, Model CDCN-106, manufactured by Omega Engineering, Inc. of Stamford, Connecticut. In use, the sensor is immersed in the process fluid and an electric current is passed from one plate through the fluid to the other plate, and the voltage across the transducer is measured.

The programming provided in the form of firmware in the program storage memory of this embodiment of the invention, although similar to that used for pH, differs with respect to the equations used to process the signals from the conductivity sensor as follows.

The conductivity sensor may be described by a constant, K, which is equal to the distance separating the plates divided by the effective area of one plate. In the simplified case of two identical flat parallel plates with only process fluid therebetween, the equation for K takes the form:

$$K = L/A$$

where
A = Area of one of the plates
L = Distance separating the plates.

Typically, the geometry of a conductivity sensor (or "cell") in actual applications is more complex than the foregoing simplified case. A common arrangement of the plates of the conductivity cell comprises concentric cylinders. For such a cell, the equation for K becomes somewhat more complex, but may still be determined either mathematically from the geometry or empirically.

In operation, an alternating current (AC) of known magnitude, and frequency typically between 50 and 10,000 Hertz, is applied to the sensor plates, and the resulting voltage across the plates is measured. Conversely, a voltage may be applied between the plates, and the resulting current through the sensor measured. In either case, the conductivity of the process fluid, C, may be calculated as:

$$C = K \cdot I/V$$

where
C = Process fluid conductivity in Siemens/cm
K = Cell constant
I = Current through cell
V = Voltage across cell plates
and solution resistivity may be calculated as:

$$R = 1/C$$

where
R = Resisitivity of process fluid in Ohm-cm.

It will be understood from the foregoing that whereas in pH measurement a chemically-induced D.C. voltage signal is generated by the electrodes and measured directly, in solution conductivity measurement the sensor is excited by an A.C. source of known magnitude. The use of A.C. voltages and currents is necessitated by the significant error voltage or current resulting from chemical reactions at the sensor plates were D.C. voltage and current to be used.

When the conductivity sensor is excited by an A.C. source, the resulting signal which develops across the conductivity sensor terminals is a linear function of the ability of the process fluid to pass electric current, or conductivity. As shown in FIG. 11, the fluid condition monitoring assembly (to right of dashed line) of this embodiment includes suitable signal conditioning electronics, as well as an A.C. signal source and detector.

The solution conductivity electrode station shown in FIG. 11 also includes a temperature sensor. Although temperature measurement is not required in order to measure simple solution conductivity, temperature may be employed to determine some secondary variable in cases where the content of the process stream is generally known. For example, conductivity at some reference temperature (e.g., 25° C.), which is different from the actual temperature of the fluid, may be determined. Another secondary variable which may be determined, where the content of the solution is known to be given salt plus water, is salinity. The conductivity vs. concentration and temperature curves are known for most salts of interest. Even where the specific salt is not known, salinity level may often be approximated because the curves for most common salts are fairly similar over a wide range of conductivity. The concentration of other conductive materials, such as acids and bases, may be similarly calculated.

As shown in FIG. 12, similar to the first embodiment, the user is offered the opportunity to calibrate the inputs of the electrode station when the "specify conductivity analyzer operation" command is given via keypad 17. With the conductivity electrode station, however, only one calibration point is needed. The electrodes are placed in a solution of known conductivity, the conductivity (and optionally temperature) is recorded, and the gain constant is calculated.

The solution conductivity monitoring capability of the apparatus of FIGS. 11 and 12 permits the user to monitor conductivity of the fluid in the wastewater stream, and/or other secondary variables as described above. As shown in FIG. 12, the user can set the desired conductivity recording interval as desired.

Similar to the foregoing embodiments, the fourth embodiment of the invention provides the unique capability of triggering sampling operations on the basis of a given fluid condition, i.e., solution conductivity (or resistivity) in this embodiment. The user can instruct the apparatus to initiate the sampler program on the basis of predetermined solution conductivity level(s). As shown in the leftmost column of FIG. 12, the user is prompted to "Set Conductivity Level(s) to Initiate Sampler Program", and the pION level(s) which the user inputs is stored in RAM along with other user inputs. Should an out-of-tolerance condition be detected during solution conductivity monitoring operations, such as where conductivity falls outside a predetermined range set by the user, or above or below a given level set by the user, the apparatus will automatically initiate sample collection. Also similar to the above embodiments, the present embodiment may be instructed to initiate the sampler program on the basis of time and/or fluid flow (see FIG. 12), and the user may access stored sampler program and/or conductivity data by requesting either that it be displayed on alphanumeric display 18 or transmitted electronically to the data transfer unit for subsequent analysis, permanent storage or obtaining a hard copy (see FIG. 11).

4. Turbidity

Figure 13:
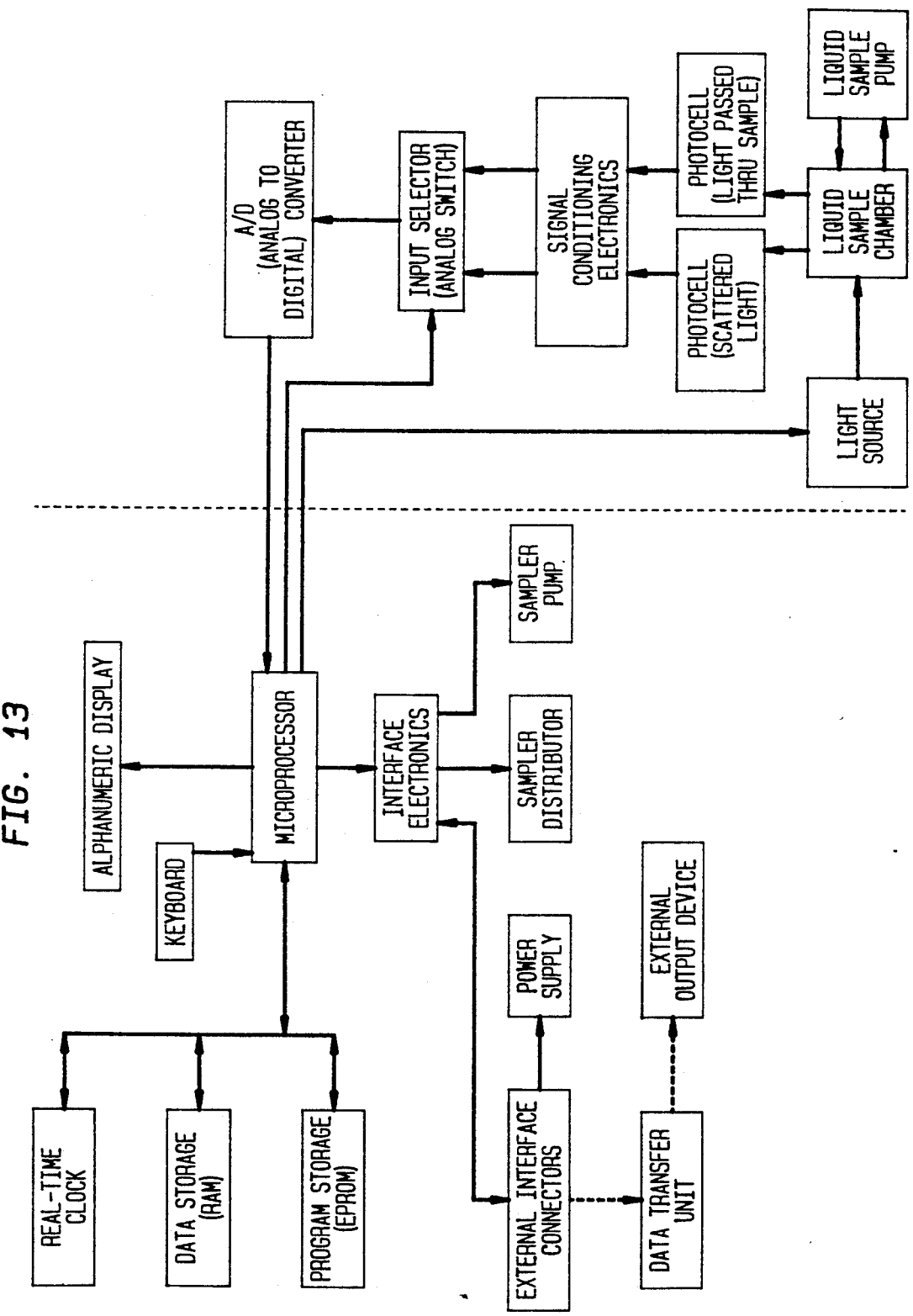
FIG. 13 is a block diagram of the various components of a fifth embodiment of the invention wherein the fluid condition monitored is turbidity.
Figure 14B:
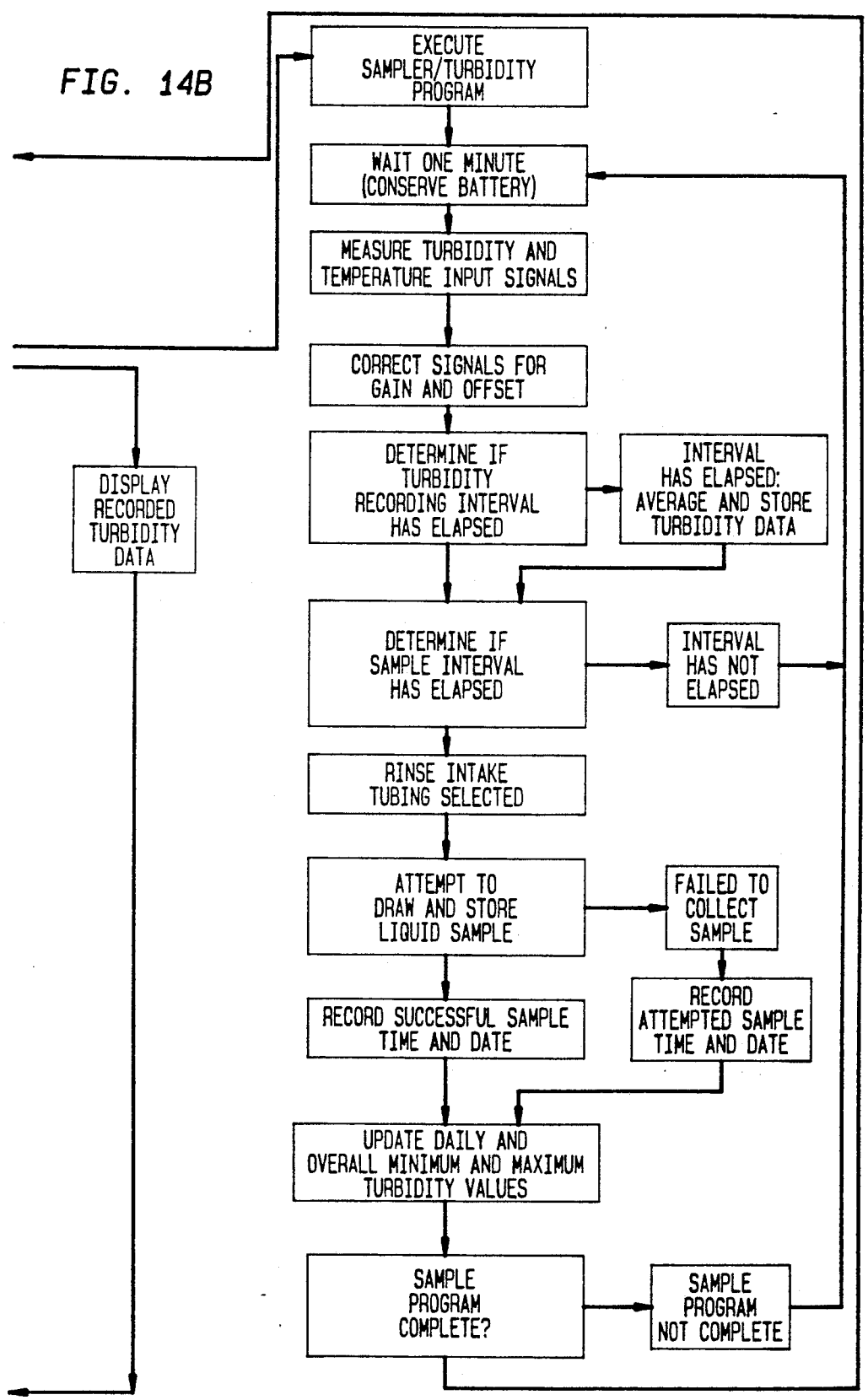

The fifth embodiment of the invention shown in FIGS. 13 and 14 provides an automatic fluid sampling and turbidity monitoring apparatus, i.e., the fluid condition monitored by the apparatus is turbidity.

Turbidity is a measure of the quantity of suspended solids in a fluid sample, and is often used as an indication of the cleanliness of both potable water sources and wastewater effluent. Unlike the chemical technique described above for measuring pH, an optical technique (described below) is used for measuring turbidity. The electronics for interfacing the sensor (signal conditioning electronics) are also substantially modified in this embodiment, as is the programming in the form of firmware which allows the microprocessor to calculate turbidity on the basis of signals received from the fluid condition monitoring assembly.

As shown to the right of the dashed line in FIG. 13, the turbidity sensor of the fluid condition monitoring assembly according to this embodiment includes a light source, a liquid sample chamber, a photocell for measuring scattered light, and a photocell for measuring light passed through a sample. Typically, the light source, liquid sample chamber and photocells are arranged in a black box having intake and outlet tubes. Light is directed through a flowing sample of the process fluid in the liquid sample chamber (typically a glass tube), with a lens provided between the light source and sample chamber for focusing the light through the sample. The first photocell, or photodetector, measures the amount of light scattered by particles suspended in the fluid, and the second photodetector measures the light passing directly through the sample for compensation purposes. As shown in FIG. 13, a liquid sample pump may also be included for providing a continuous flowing sample to the sample chamber.

An improved technique for measuring turbidity is provided in U.S. E.P.A. Method 180.1. According to the E.P.A. specification, light in the visible portion of the spectrum is used. An example of one of the many commercially-available turbidity instruments suitable for use with the invention, and approved by the E.P.A., is the Ratio 2000 Turbidimeter, Model 42100, manufactured by Hach Company of Loveland, Colo.

The interface means for the turbidity sensor, shown in FIG. 13, includes signal conditioning electronics which receives signals from both photocells and converts such signals to a voltage signal of suitable amplitude for the A/D converter. As described above with respect to the first embodiment, an analog switch is provided for presenting one signal at a time to the A/D converter.

The firmware of the microprocessor in this embodiment is similar in many respects to that described above for pH. The principal difference is that the equations used to process the raw photodetector data into turbidity information are substantially different from the equations used for processing data from the pH electrodes, and temperature is not employed in measuring turbidity. The programming for turbidity measurement involves known techniques for measuring the ratio of the intensities of the transmitted and the incident light, with a relation between absorbance and concentration of the suspended material being derived therefrom.

As in the foregoing embodiments, the user is offered the opportunity to calibrate turbidity inputs under the "Specify Turbidity Analyzer Operation" sequence of user prompts. To calibrate the turbidity inputs, the user is first prompted to load the sample chamber of the turbidity sensor with a clear sample so that inputs may be recorded therefrom, and the user is then prompted to fill the sample chamber with a calibration solution so that inputs may be recorded and turbidity gain and offset constants calculated.

The turbidity monitoring capability of the apparatus of FIGS. 13 and 14 permits the user to verify that an acceptable turbidity level is maintained in the wastewater stream. As shown in FIG. 14, the user can set the desired turbidity recording interval as desired.

Similar to the foregoing embodiments, the fifth embodiment of the invention provides the unique capability of triggering sampling operations on the basis of a given fluid condition, i.e., turbidity in this embodiment. The user can instruct the apparatus to initiate the sampler program on the basis of predetermined turbidity level(s). As shown in the leftmost column of FIG. 14, the user is prompted to "Set Turbidity Level(s) to Initiate Sampler Program", and the turbidity level(s) which the user inputs is stored in RAM along with other user inputs. Should an out-of-tolerance condition be detected during turbidity monitoring operations, such as where turbidity rises above a pre-set level, the apparatus will automatically initiate sample collection. Also similar to the above embodiments, the present embodiment may be instructed to initiate the sampler program on the basis of time and/or fluid flow (see FIG. 14), and the user may access stored sampler program and/or turbidity data by requesting either that it be displayed on alphanumeric display 18 or transmitted electronically to the data transfer unit for subsequent analysis, permanent storage or obtaining a hard copy (see FIG. 9).

5. Dissolved Oxygen

Figure 15:
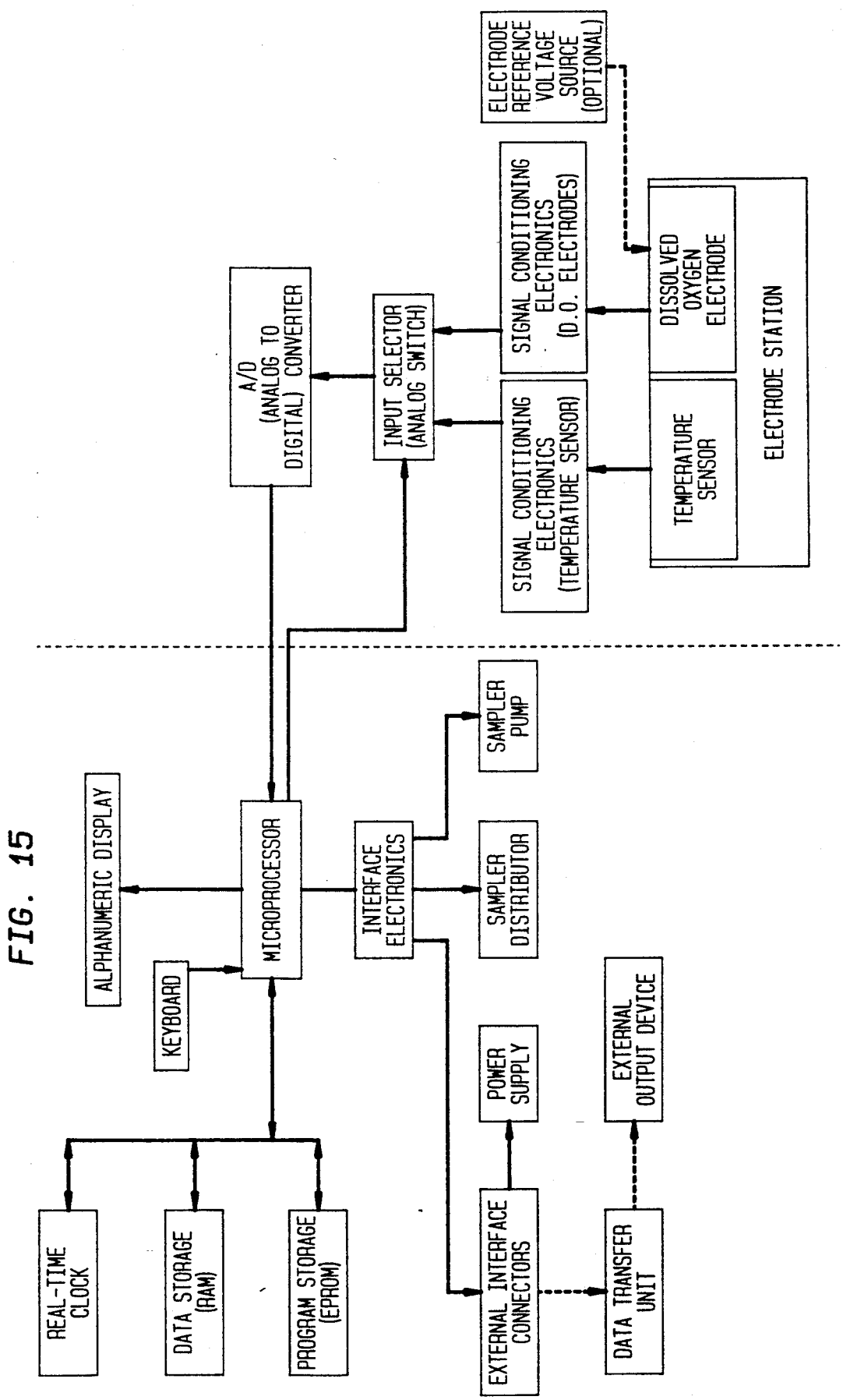
FIG. 15 is a block diagram of the various components of a sixth embodiment of the invention wherein the fluid condition monitored is dissolved oxygen.
Figures 16, 16A:
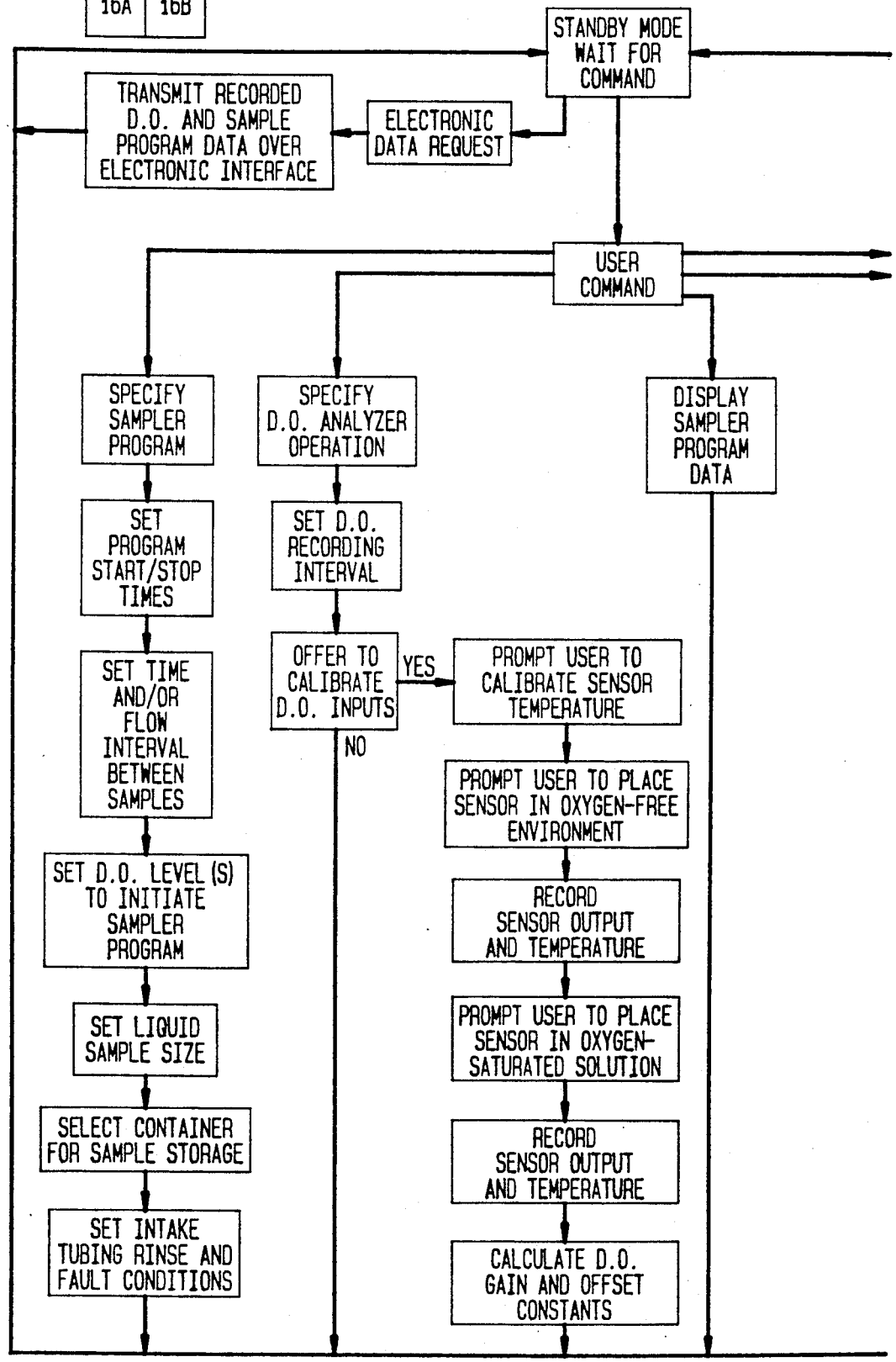
FIGS. 16a and 16b are a flow chart showing operational sequences of the apparatus according to the sixth embodiment shown in FIG. 15.
Figure 16B:
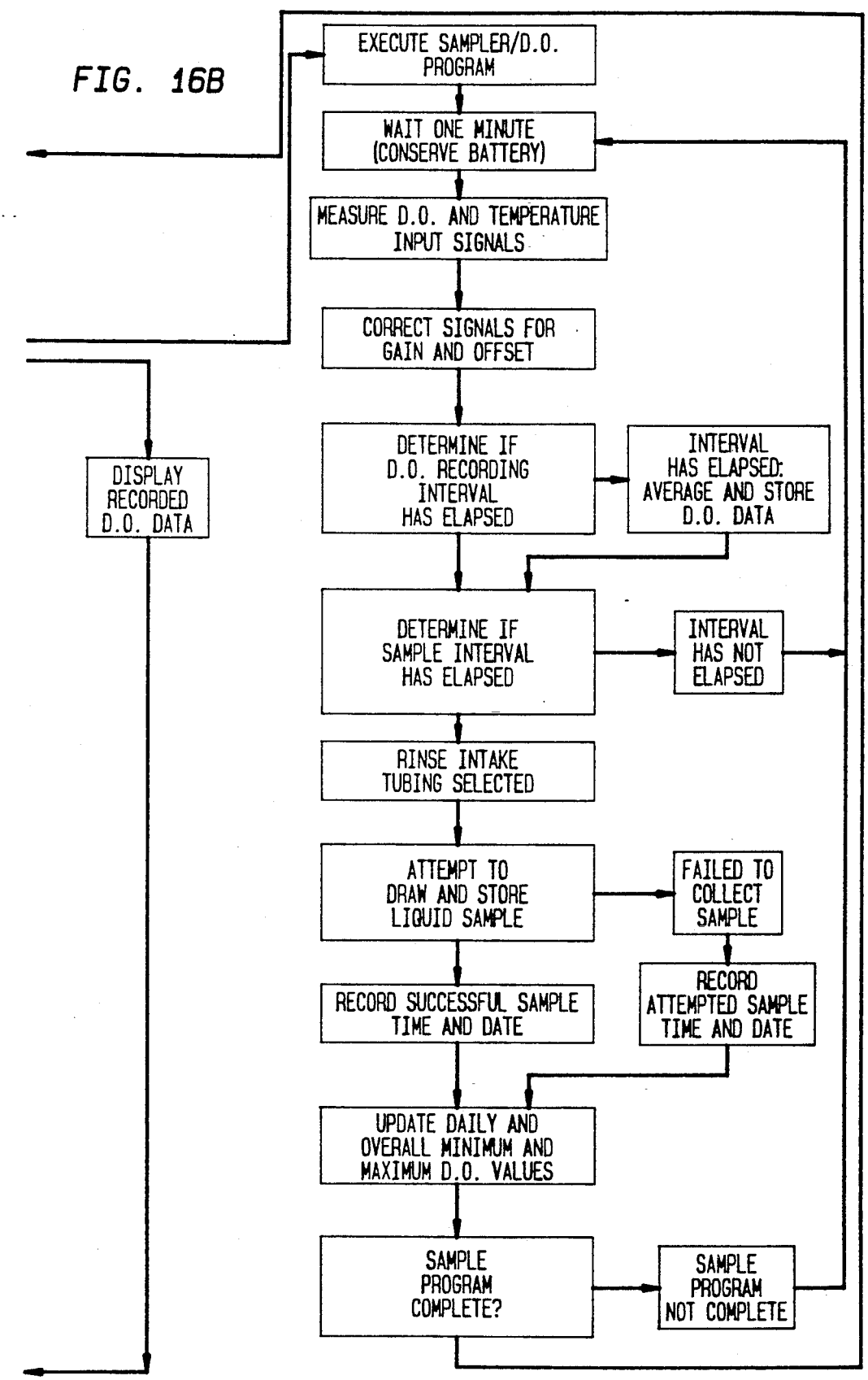

The sixth embodiment of the invention shown in FIGS. 15 and 16 provides an automatic fluid sampling and dissolved oxygen monitoring apparatus, i.e., the fluid condition monitored by the apparatus is dissolved oxygen.

In this embodiment the sensor 30 of FIG. 6 comprises either a polarographic type or galvanic type dissolved oxygen sensor. The electronics for interfacing the sensor are also modified in this embodiment, as is the programming which allows the microprocessor to calculate the dissolved oxygen level on the basis of signals received from the fluid condition monitoring assembly.

Monitoring of dissolved oxygen, a measure of the partial pressure of oxygen in a fluid generally expressed in units of Atmospheres (atm.), is of considerable practical utility because oxygen is a basic requirement for many biological activities. For example, where wastewater treatment processes employ aerobic bacteria to break down organic compounds, the level of dissolved oxygen can be used to determine the effectiveness of the process.

With reference to FIG. 15, wherein the fluid condition monitoring assembly of this embodiment is shown to the right of the dashed line, the dissolved oxygen sensor (or electrode station) comprises a dissolved oxygen electrode, and a temperature sensor. More specifically, the dissolved oxygen sensor comprises an electrochemical cell which is typically isolated from the process stream by a permeable membrane, such as PTFE (Teflon), which is on the order of 0.002 inch thick. In operation, oxygen diffuses across the membrane into the cell where it is chemically reduced, resulting in an electric current from the cell terminals.

Both types of commercially-available dissolved oxygen sensors, i.e., the polarographic type and the galvanic type, are suitable for use with the invention. Both sensor types are amperometric in nature, i.e., they provide an electric current output proportional to the partial pressure of oxygen present in the process stream. In the galvanic sensor, a voltage is generated internally to produce an output current. In the polarographic sensor, an external voltage source is required. To this end, FIG. 15 depicts as part of the interface electronics an optional electrode reference voltage source.

By way of example, one of the many commercially-available dissolved oxygen sensors suitable for use with the invention is the wastewater dissolved oxygen sensor, Model $DO_2$-WW, manufactured by Innovative Sensors, Inc. of Anaheim, Calif.

The output from a dissolved oxygen sensor may be expressed in general form as:

$$I=(K)(A)(D)(S)(pO2)/(Z)$$

where
I = Sensor output current
K = Constant determined by sensor construction
A = Area of sensor cathode
D = Permeability coefficient of sensor membrane
S = Solubility coefficient of sensor membrane
Z = Membrane thickness
pO2 = Partial pressure of oxygen in process stream.

For practical purposes, taking into account the dependency of the membrane permeability coefficient (D) on temperature, the sensor output may be characterized as:

$$I=(pO2)(A)\exp(-J/T)$$

where
A,J = Constants determined by cell construction
T = Temperature in degrees Kelvin.
A typical full scale cell output is 10 microamperes at 0.21 atm. partial pressure of oxygen and 30 degrees Celsius.

With reference to FIG. 15, the interface circuitry including signal conditioning electronics for the dissolved oxygen sensor must convert the rather small output current signal from the sensor to a voltage signal which is then amplified to a level suitable for input to the A/D converter. As described above, an optional voltage source may be provided for accommodating a polarographic type sensor. Further, as described above with respect to pH measurement, signal conditioning electronics are provided for converting output from the temperature sensor to a voltage signal of suitable amplitude for the A/D converter. As with the pH sensor, temperature measurement is required in order to compensate for changes in the dissolved oxygen sensor output with temperature.

With reference to FIG. 16, the programming provided in the form of firmware in the program storage memory of this embodiment of the invention, although similar to that used for pH, differs with respect to the equations used to process the signals from the dissolved oxygen sensor, and with respect to calibration.

As shown in FIG. 16, similar to the foregoing embodiments, the user is offered the opportunity to calibrate the inputs of the dissolved oxygen electrode station when the "specify conductivity analyzer operation" command is given via keypad 17. To calibrate the dissolved oxygen inputs, the user is first prompted to calibrate the sensor temperature and then to place the sensor in an oxygen-free environment, with sensor output and temperature being recorded. The user is next prompted to place the sensor in an oxygen-saturated solution, with sensor output and temperature again being recorded and dissolved oxygen gain and offset constants calculated.

The dissolved oxygen monitoring capability of the apparatus of FIGS. 15 and 16 permits the user to monitor dissolved oxygen in the wastewater stream. As shown in FIG. 16, the user can set the desired dissolved oxygen recording interval as desired.

As in the foregoing embodiments, the dissolved oxygen embodiment of the invention provides the unique capability of triggering sampling operations on the basis of a given fluid condition, in this case dissolved oxygen level. The user can instruct the apparatus to initiate the sampler program on the basis of predetermined dissolved oxygen level(s). As shown in the leftmost column of FIG. 16, the user is prompted to "Set D. O. Level(s) to Initiate Sampler Program", and the dissolved oxygen level(s) which the user inputs is stored in RAM along with other user inputs. Should an out-of-tolerance condition be detected during dissolved oxygen monitoring operations, such as where dissolved oxygen falls below a predetermined level set by the user, the apparatus will automatically initiate sample collection. Also similar to the above embodiments, the present embodiment may be instructed to initiate the sampler program on the basis of time and/or fluid flow (see FIG. 16), and the user may access stored sampler program and/or conductivity data by requesting either that it be displayed on alphanumeric display 18 or transmitted electronically to the data transfer unit for subsequent analysis, permanent storage or obtaining a hard copy (see FIG. 15).

It will be understood from the foregoing that the essential differences between the various embodiments of the invention reside in the type of sensor used and the interface electronics therefor, and programming modifications. The invention contemplates that the apparatus according to the invention may be adapted to monitor a number of different fluid conditions, and to trigger sampler program operation on the basis of any desired one(s) of such conditions. To this end, the program storage memory in the form of pre-installed EPROM chips may be programmed to perform the calculations necessary for a variety of different fluid conditions, and to allow for necessary calibration. As such, the program storage memory can be programmed to have a relatively universal capacity capable of processing inputs from a variety of different fluid condition sensors. A skilled technician could then convert the fluid condition monitoring assembly of the apparatus from one type to the other merely by replacing the circuit board containing the sensor interface electronics, as needed, to accommodate different sensors. Alternatively, the apparatus could be pre-equipped with more than one such circuit board so as to be inherently capable of monitoring more than one fluid condition as desired, and of triggering sampling operations on the basis of more than one fluid condition.

It will also be understood that the invention is not limited to the particular fluid conditions and sensors described above, and other suitable known sensors and corresponding interface electronics and programming may alternatively be employed for monitoring other conditions. For example, the apparatus could be adapted to monitor total organic carbon levels, and to trigger sample collection on the basis of predetermined levels, by employing a total organic carbon sensor and suitable interface electronics and programming.

In use, the apparatus according to any of the embodiments of the invention can be conveniently transported for mounting in sewer manholes, or to remote sites for use in other types of applications. When used in a sewer manhole, the apparatus can be conveniently mounted as a single unitary structure above an open flowing sewer passage. The apparatus is mounted for use by: connecting the sensor with one of the connectors 16; connecting the fluid intake conduit 9 with the pump 8; appropriately mounting the sensor relative to the fluid in the channel; positioning the weighted strainer 12 at the end of conduit 9 within the fluid in the channel; and suspending the unit from the upper end of the manhole (FIG. 6).

The integral unit includes all the electronics, computer programming, and hardware required for fully automatic sampling and fluid condition monitoring, as well as storage of sampling and fluid condition data for later retrieval. The unit can be user-programmed to collect samples at desired time intervals; or when the calculated values of a given fluid condition falls outside a predetermined range, or above or below a predetermined level; or on the basis of some combination of both criteria. The stored data will reflect the time and date of each sample, the value of the fluid condition (such as pH level) at user-selected intervals, as well as the various other parameters described above. The user can call the data up for display on the alphanumeric display of the unit, and/or can transfer the data to a remote output device via the portable data transfer unit. Transfer of the data via the data transfer unit permits recording of the data in hard copy form via a printer, permanent storage of the data in a database, and/or manipulation of the data for statistical analyses, etc., via a conventional software program.

It will be further understood that the integral fluid sampling and fluid condition monitoring apparatus of the invention may be selectively employed for use for sampling and fluid condition monitoring both, for sampling only, or for monitoring one or more fluid conditions only, as desired. The independent operation of either the sampling assembly or the fluid condition monitoring assembly can be effected via user input to the computer control means according to the invention.

While there have been described hereinabove what are at present considered to be the preferred embodiments of the invention, it will be understood that various modifications may be made therein without departing from the spirit and scope of the invention. The present embodiments are therefore to be considered in all respects as illustrative, and not restrictive. The scope of the invention is indicated by the appended claims rather than by the foregoing description.

We claim:

1. An apparatus for automatically collecting samples from a fluid channel and for monitoring a fluid condition, according to modes of operation selected by a user, said modes of operation including sampling on the basis of time and/or at least one predetermined value of said fluid condition being monitored, comprising:
    means for controlling said apparatus;
    a fluid sampling assembly having an inlet for receiving fluid from said channel;
    power means for supplying power to each element of said apparatus;
    said fluid sampling assembly, said control means and said power means comprising an integral operating unit disposed within a single case, said case being sufficiently compact so as to be receivable in a manhole;
    said fluid condition being monitored comprises a fluid condition other than flow rate;
    said integral operating unit further including at least one input connection for receiving at least one detected signal related to said fluid condition; and
    said control means comprising a microprocessor, program memory and data memory, wherein:
        said program memory is programmed for computing values of said fluid condition;
        said data memory stores user-selected input parameters including operating mode selection data, said at least one predetermined value of said fluid condition, and sampling times;
        said microprocessor receives said at least one signal related to said fluid condition via said input connection and utilizes said program memory to calculate values of said fluid condition based on said at least one signal;
        said microprocessor controls said fluid sampling assembly according to at least one of said modes of operation selected by the user, based on said user input sampling times and/or a deviation of computed values of said fluid condition from said user-selected predetermined value of said fluid condition; and
        said data memory stores fluid sampling data and fluid condition data.

2. An apparatus according to claim 1, wherein:
    said apparatus further comprises means for conditioning said at least one signal for input to said control means; and
    said integral operating unit further comprises means for displaying said stored fluid sampling data and fluid condition data.

3. An apparatus according to claim 2, wherein:

said display means comprises an alphanumeric display mounted to said case so as to be visible to a user; and said apparatus further comprises user keypad means, mounted to said case and communicating with said data memory, for entering said user-selected input parameters and for retrieving said fluid sampling data and fluid condition data stored in said data memory by a user command to display said data on said alphanumeric display.

4. An apparatus according to claim 1, further comprising:

means for selectively transferring said stored data to an external output device, said transfer means being controlled by said microprocessor.

5. An apparatus according to claim 1, wherein:

said user-selected input parameters further comprise program start and stop criteria, fluid sample size, sample container selection, and intervals and units for storing fluid condition data.

6. An apparatus according to claim 1, further comprising:

sensor means for producing said at least one detected signal related to said fluid condition when said sensor is mounted in a detecting position relative to said fluid channel, said sensor means being selectively connectable to said at least one input connection of said integral operating unit.

7. An apparatus according to claim 6, wherein:

said program memory stores a program for prompting a user to perform a calibration procedure for said sensor means, and further stores equations for calculating calibration data for use by said microprocessor in calculating values of said fluid condition based on said at least one signal.

8. An apparatus according to claim 6, wherein:
said fluid condition comprises pH; and
said sensor means comprises at least a pH electrode, a reference electrode and a temperature sensor.

9. An apparatus according to claim 6, wherein:
said fluid condition comprises oxidation reduction potential; and
said sensor means comprises an oxidation reduction potential electrode and a reference electrode.

10. An apparatus according to claim 6, wherein:
said fluid condition comprises the activity of a specific ion; and
said sensor means comprises at least a specific ion electrode, a reference electrode and a temperature sensor.

11. An apparatus according to claim 6, wherein:
said fluid condition comprises solution conductivity; and
said sensor means comprises a conductivity sensor and a temperature sensor.

12. An apparatus according to claim 6, wherein:
said fluid condition comprises turbidity; and
said sensor means comprises a sample chamber, means for directing light through said sample chamber, and photocell means, disposed adjacent said sampler chamber, for measuring scattered light therefrom.

13. An apparatus according to claim 12, further comprising:

pump means operatively cooperating with said sample chamber to supply a constantly flowing sample through said chamber.

14. An apparatus according to claim 6, wherein:
said fluid condition comprises dissolved oxygen; and
said sensor means comprises a dissolved oxygen electrode, a reference electrode and a temperature sensor.

15. An apparatus according to claim 1, wherein:
said data memory is provided with back-up battery power means for permitting said stored data to remain stored in memory when said main power means of said apparatus is turned off.

16. An apparatus according to claim 1, wherein:
said microprocessor automatically initiates fluid sample collection by said fluid sampling assembly when a present calculated value of said fluid condition deviates from said at least one predetermined value of said fluid condition by exceeding a predetermined value.

17. An apparatus according to claim 1, wherein:
said microprocessor automatically initiates fluid sample collection by said fluid sampling assembly when a present calculated value of said fluid condition deviates from said at least one predetermined value of said fluid condition by falling below a predetermined value.

18. An apparatus according to claim 1, wherein:
said at least one predetermined value of said fluid condition comprises a pair of values defining an acceptable range for said fluid condition; and
said microprocessor automatically initiates fluid sample collection by said fluid sampling assembly when a present calculated value of said fluid condition is outside said acceptable range of values of said fluid condition.

19. An apparatus according to claim 1, further comprising:

a flow meter;
said microprocessor being selectively connectable with said flow meter so as to receive signals therefrom; and wherein
said modes of operation further include sampling on the basis of flow rate; and
said microprocessor controls said fluid sampling assembly according to at least one of said modes of operation selected by the user, based on said user input sampling times, said deviation of said computed values of said fluid condition from said user-selected predetermined value of said fluid condition, and/or flow rate.

20. An apparatus according to claim 6, further comprising:

a fluid sample intake conduit which extends to fluid in said channel, said sample intake conduit being selectively connectable to said fluid sampling assembly inlet; and
said user-selected input parameters further comprising data relating to the volume of said sample intake conduit and purging thereof.

21. A method for automatically collecting samples from a fluid channel and for monitoring a fluid condition, according to modes of operation selected by a user, said modes of operation including sampling on the basis of time and/or at least one predetermined value of said fluid condition being monitored, comprising the steps of:

connecting, to an input connection of an integral operating unit, a sensor means for detecting a variable related to a fluid condition other than flow rate;

connecting a sample intake conduit to an inlet of a sampling assembly of said integral operating unit;

mounting said sensor means in a detecting position relative to said channel;

lowering a lower intake end of said sample intake conduit into said fluid in said channel;

positioning in an operable position said integral operating unit, including said fluid sampling assembly, means for supplying power to said integral operating unit, and means for controlling said integral operating unit, all disposed within a single case which is sufficiently compact so as to be receivable in a manhole;

operating said control means, including program memory thereof which is programmed for computing values of said fluid condition, and data memory thereof which stores user-selected input parameters including operating mode selection data, said at least one predetermined value of said fluid condition and fluid sampling times, such that a microprocessor of said control means receives said signal related to said fluid condition from said sensor means via said input connection and utilizes said program memory to calculate values of said fluid condition based on said signal, for controlling said fluid sampling assembly according to at least one of said modes of operation selected by the user, based on said user input sampling times and/or a deviation of computed values of said fluid condition from said user-selected predetermined value of said fluid condition; and operating said data memory of said control means for automatically storing fluid sampling data and fluid condition data.

22. A method according to claim 21, further comprising the steps of:

inputting user commands, via a user input keypad means of said integral operating unit, relating to parameters including sample collection time intervals, said at least one predetermined value of said fluid condition, program start and stop criteria, sample size, sample container selection, and data relating to the volume of said sample intake conduit and purging thereof.

23. A method according to claim 21, further comprising the step of:

displaying the stored fluid sampling data and fluid condition data on an alphanumeric display of said integral operating unit, in response to a user display command input via said keypad means.

24. A method according to claim 22, further comprising the step of:

transferring the stored fluid sampling data and fluid condition data to a portable data transfer unit by selectively connecting said transfer unit to a connector connected with said microprocessor and inputting a command to transfer said data to said transfer unit.

25. A method according to claim 24, further comprising the step of:

after said transferring step, connecting said portable data transfer unit to an auxiliary output device and inputting a command to transfer said data from said transfer unit to said output device.

26. An apparatus for automatically collecting samples from a fluid channel, for measuring a fluid flow-related variable, and for monitoring a fluid condition other than flow rate, according to modes of operation selected by a user, said modes of operation including sampling on the basis of time, said fluid flow-related variable, and/or said fluid condition being monitored, comprising:

means for controlling said apparatus;

a fluid sampling assembly having an inlet for receiving fluid from said channel;

power means for supplying power to each element of said apparatus;

said fluid sampling assembly, said control means, and said power means comprising an integral operating unit disposed within a single case, said case being sufficiently compact so as to be receivable in a manhole;

said integral operating unit including a first input connection for receiving a detected signal related to fluid flow in said channel, and a second input connection for receiving at least one detected signal related to said fluid condition; and said control means comprising a microprocessor, program memory and data memory, wherein:

said program memory is programmed for computing values of said fluid condition, and is programmed for computing values of said fluid flow-related variable;

said data memory stores user-selected input parameters including operating mode selection data, at least one fluid flow-related parameter, at least one predetermined value of said fluid condition, and sampling times;

said microprocessor receives said signal related to fluid flow via said first input connection and utilizes said program memory to calculate a value of said fluid flow-related variable based on said signal and said at least one user-selected fluid flow-related parameter;

said microprocessor receives said at least one signal related to said fluid condition via said second input connection and utilizes said program memory to calculate values of said fluid condition based on said at least one signal;

said microprocessor controls said fluid sampling assembly according to at least one of said modes of operation selected by the user, based on said user input sampling times, computed values of said fluid flow-related variable, and/or a deviation of computed values of said fluid condition from said user-selected predetermined value of said fluid condition; and said data memory stores fluid sampling data, fluid flow-related data, and fluid condition data.

27. An apparatus according to claim 26, wherein:

said apparatus further comprises first conditioning means for conditioning said signal related to fluid flow for input to said control means, and second conditioning means for conditioning said at least one signal related to said fluid condition for input to said control means;

said at least one user-selected fluid flow-related parameter comprises data relating to the size and type of fluid channel from which fluid samples are collected; and said fluid flow-related variable comprises the fluid flow rate in said channel.

28. An apparatus according to claim 26, further comprising:

means for selectively transferring said stored data to an external output device, said transfer means being controlled by said microprocessor, and wherein said integral operating unit further comprises means for displaying said stored data.

29. An apparatus according to claim 26, further comprising:

first sensor means for producing said signal related to fluid flow in said channel when said sensor is mounted in a detecting position relative to said channel, said first sensor means being selectively connectable to said first input connection of said integral operating unit;

second sensor means for producing said at least one signal related to said fluid condition, said second sensor means being selectively connectable to said second input connection of said integral operating unit; and a fluid sample intake conduit which extends to fluid in said channel, said sample intake conduit being selectively connectable to said fluid sampling assembly inlet.

* * * * *

UNITED STATES PATENT AND TRADEMARK OFFICE
CERTIFICATE OF CORRECTION

PATENT NO. : 5,172,332
DATED : December 15, 1992
INVENTOR(S) : Hungerford et al.

It is certified that error appears in the above-identified patent and that said Letters Patent is hereby corrected as shown below:

Column 4, line 34, after "principal" insert --object--.

Signed and Sealed this

Nineteenth Day of October, 1993

Attest:

BRUCE LEHMAN

*Attesting Officer*          *Commissioner of Patents and Trademarks*